(12) United States Patent
Kim et al.

(10) Patent No.: US 6,861,415 B2
(45) Date of Patent: Mar. 1, 2005

(54) 21-SUBSTITUTED PROGESTERONE DERIVATIVES AS NEW ANTIPROGESTATIONAL AGENTS

(75) Inventors: Hyun K. Kim, Bethesda, MD (US); Richard P. Blye, Highland, MD (US); Pemmaraju N. Rao, San Antonio, TX (US); James W. Cessac, San Antonio, TX (US); Carmie K. Acosta, San Antonio, TX (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/180,132

(22) PCT Filed: Apr. 30, 1997

(86) PCT No.: PCT/US97/07373
§ 371 (c)(1),
(2), (4) Date: May 24, 1999

(87) PCT Pub. No.: WO97/41145
PCT Pub. Date: Nov. 6, 1997

(65) Prior Publication Data
US 2002/0025951 A1 Feb. 28, 2002

Related U.S. Application Data
(60) Provisional application No. 60/016,628, filed on May 1, 1996.

(51) Int. Cl.$^7$ ............................. A61K 31/56; C07J 5/00; C07J 9/00
(52) U.S. Cl. ................. 514/179; 514/182; 514/841; 552/556; 552/595; 552/598; 552/602; 552/608
(58) Field of Search ............................. 514/169, 177, 514/179, 182; 552/520, 540, 544, 548, 552, 553, 554, 555, 556, 595, 598, 602–608

(56) References Cited

U.S. PATENT DOCUMENTS

| | | | |
|---|---|---|---|
| 4,386,085 A | 5/1983 | Teutsch et al. | 424/238 |
| 4,477,445 A | 10/1984 | Philibert et al. | 424/239 |
| 4,634,695 A * | 1/1987 | Torelli et al. | 514/178 |
| 4,808,710 A | 2/1989 | de Jongh et al. | 540/30 |
| 4,912,097 A | 3/1990 | Teutsch et al. | 514/172 |
| 4,921,845 A | 5/1990 | de Jongh et al. | 514/172 |
| 4,943,566 A | 7/1990 | Nedelec et al. | 514/179 |
| 4,954,490 A | 9/1990 | Cook et al. | 514/176 |
| 5,064,822 A | 11/1991 | Philibert et al. | 514/172 |
| 5,073,548 A | 12/1991 | Cook et al. | 514/169 |
| 5,089,488 A | 2/1992 | Ottow et al. | 514/179 |
| 5,166,199 A | 11/1992 | Kasch et al. | 514/169 |
| 5,173,483 A | 12/1992 | Grandadam | 514/178 |
| 5,272,140 A | 12/1993 | Loozen | 514/172 |
| 5,364,847 A | 11/1994 | Labrie et al. | 514/182 |
| 5,426,102 A | 6/1995 | Schwede et al. | 514/173 |
| 5,446,036 A * | 8/1995 | Scholz et al. | 514/175 |
| 5,741,787 A * | 4/1998 | Peeters | 514/177 |

FOREIGN PATENT DOCUMENTS

| | | |
|---|---|---|
| CA | 1307784 | 9/1992 |
| EP | 057 115 | 8/1982 |
| EP | 129 499 | 6/1984 |
| EP | 136 586 | 9/1984 |
| WO | WO 89/12448 | 12/1989 |

OTHER PUBLICATIONS

Cook, et al., *Life Sciences*, 52(2):155–162 (1993).
Cook, et al., *J. Steroid Biochem.*, vol. 25, Abstract 365 (1986).
Heikinheimo, et al., *J. Steroid Biochem.*, 26(2):279–284 (1987).
Horwitz, *Endocrinology*, 116(6):2236–2245 (1985).
Kloosterboer, et al., *J. steroid Biochem.*, 31(4B):567–571 (1988).
Livingston, et al., *J. Am. Chem. Soc.*, 112:6449–6450 (1990).

(List continued on next page.)

*Primary Examiner*—Barbara P. Badio
(74) *Attorney, Agent, or Firm*—Townsend and Townsend and Crew LLP

(57) ABSTRACT

A compound having the general formula:

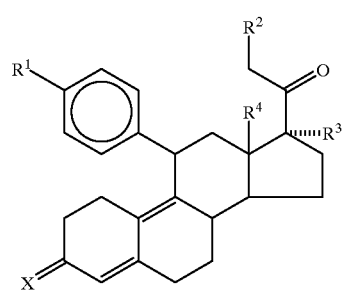

in which: $R^1$ is a member selected from the group consisting of —$OCH_3$, —$SCH_3$, —$N(CH_3)_2$, —$NHCH_3$, —CHO, —$COCH_3$ and —$CHOHCH_3$; $R^2$ is a member selected from the group consisting of halogen, alkyl, acyl, hydroxy, alkoxy, acyloxy, alkyl carbonate, cypionyloxy, S-alkyl and S-acyl; $R^3$ is a member selected from the group consisting of alkyl, hydroxy, alkoxy and acyloxy; $R^4$ is a member selected from the group consisting of hydrogen and alkyl; and X is a member selected from the group consisting of =O and =N—$OR^5$, wherein $R^5$ is a member selected from the group consisting of hydrogen and alkyl.

In addition to providing the compounds of Formula I, the present invention provides methods wherein the compounds of Formula I are advantageously used, inter alia, to antagonize endogenous progesterone; to induce menses; to treat endometriosis; to treat dysmenorrhea; to treat endocrine hormone-dependent tumors; to treat uterine fibroids; to inhibit uterine endometrial proliferation; to induce labor; and for contraception.

36 Claims, 5 Drawing Sheets

OTHER PUBLICATIONS

Livingston, *Adv. Med. Chem.,* *1*:137–174 (1992).
Nieman, et al., *J. Clin. Endocrin. Metab., 61*(*3*):536–540 (1985).
Spitznagle, et al., *Steroids, 30*(*4*):435–438 (1977).
Teutsch, et al., *Human Reproduction, 9*(*1*):12–31 (1994).

* cited by examiner

* Cyp = 3-Cyclopentylpropionyl-

21-SUBSTITUTED PROGESTERONE DERIVATIVES AS NEW ANTIPROGESTATIONAL AGENTS

This application claims benefit of provisional application 60/016,628 filed May 1, 1996.

FIELD OF THE INVENTION

The present invention relates generally to the field of steroids and, in particular, to new 11β-substituted-21-substituted-19-nor-progesterone analogs which possess potent antiprogestational activity with minimal antiglucocorticoid activity.

BACKGROUND OF THE INVENTION

There have been numerous attempts over the past few decades to prepare steroids with antihormonal activity. These have been reasonably successful where anti-estrogens and anti-androgens are concerned. However, the discovery of effective antiprogestational and antiglucocorticoid steroids has proved to be a formidable task for the steroid chemist. It has been generally recognized for some years, however, that antiprogestational steroids would find wide applicability in population control, while antiglucocorticoids would be extremely valuable in the treatment of, for example, Cushing's syndrome and other conditions characterized by excessive endogenous production of cortisone. In the last decade, largely through the efforts of Teutsch, et al. of the Roussel-Uclaf group in France, a new series of 19-nortestosterone derivatives has been synthesized with strong affinity for the progesterone and glucocorticoid receptors and with marked antiprogestational and antiglucocorticoid activity in vivo. This important discovery revealed the existence of a pocket in the progesterone/glucocorticoid receptors that is able to accommodate a large 11β-substituent on selected 19-nortestosterone derivatives. By suitable selection of such a substituent, steroids with antihormonal properties were obtained.

The pioneering studies of Teutsch, et al. on the synthesis of antiprogestational and antiglucocorticoid steroids is summarized in a recent review article (G. Teutsch in *Adrenal Steroid Antagonism*. Ed. M. K. Agarwal, Walter de Gruyter and Co., Berlin, 1984. pp. 43–75) describing the work leading to the discovery of RU-38,486, the first steroid of this type selected for clinical development. RU-38,486 or mifepristone was found to be an effective antiprogestational/contragestative agent when administered during the early stages of pregnancy (IPPF Medical Bulletin 20; No. 5, 1986). In addition to these antiprogestational properties, mifepristone has very significant antiglucocorticoid activity and was successfully used by Nieman, et al. (*J. Clin. Endocrinology Metab.* 61:536, 1985) in the treatment of Cushing's syndrome. In common with the vast majority of steroidal hormone analogs, mifepristone additionally exhibits a range of biological properties. Thus, for example, it exhibits growth-inhibitory properties towards estrogen-insensitive T47Dco human breast cancer cells (Horwitz, *Endocrinology* 116:2236, 1985). Experimental evidence suggests that the metabolic products derived from mifepristone contribute to its antiprogestational and antiglucocorticoid properties (Heikinheimo, et al., *J. Steroid Biochem.* 26:279, 1987).

Ideally, for purposes of contraception, it would be advantageous to have compounds which possess antiprogestational activity without (or with minimal) antiglucocorticoid activity. Although there have been a number of attempts to modify the mifepristone structure in order to obtain separation of the antiprogestational activity from the antiglucocorticoid activity, this goal has not yet been fully achieved. As such, there remains a need in the art for the development of new steroids which possess antiprogestational activity with minimal antiglucocorticoid activity.

SUMMARY OF THE INVENTION

The present invention provides new steroids which possess potent antiprogestational activity with minimal antiglucocorticoid activity. More particularly, the present invention provides compounds having the general formula:

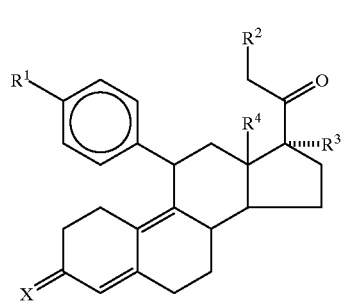

wherein: $R^1$ is a functional group including, but not limited to, —OCH$_3$, —SCH$_3$, —N(CH$_3$)$_2$, —NHCH$_3$, —CHO, —COCH$_3$ and —CHOHCH$_3$; $R^2$ is a functional group including, but not limited to, halogen, alkyl, acyl, hydroxy, alkoxy, acyloxy (e.g., acetoxy, glycinate, etc.) alkyl carbonate, cypionyloxy, S-alkyl and S-acyl; $R^3$ is a functional group including, but not limited to, alkyl (e.g., methyl, methoxymethyl, etc.), hydroxy, alkoxy (e.g., methoxy, ethoxy, methoxyethoxy, etc.), and acyloxy; $R^4$ is a functional group including, but not limited to, hydrogen and alkyl; and X is a functional group including, but not limited to, =O and =N—OR$^5$, wherein $R^5$ is a member selected from the group consisting of hydrogen and alkyl.

In addition to providing compounds of Formula I, the present invention provides methods wherein the compounds of Formula I are advantageously used, inter alia, to antagonize endogenous progesterone; to induce menses; to treat endometriosis; to treat dysmenorrhea; to treat endocrine hormone-dependent tumors; to treat uterine fibroids; to inhibit uterine endometrial proliferation; to induce labor; and for contraception.

Other features, objects and advantages of the invention and its preferred embodiments will become apparent from the detailed description which follows.

DETAILED DESCRIPTION OF THE INVENTION AND PREFERRED EMBODIMENTS

Figure 1A:
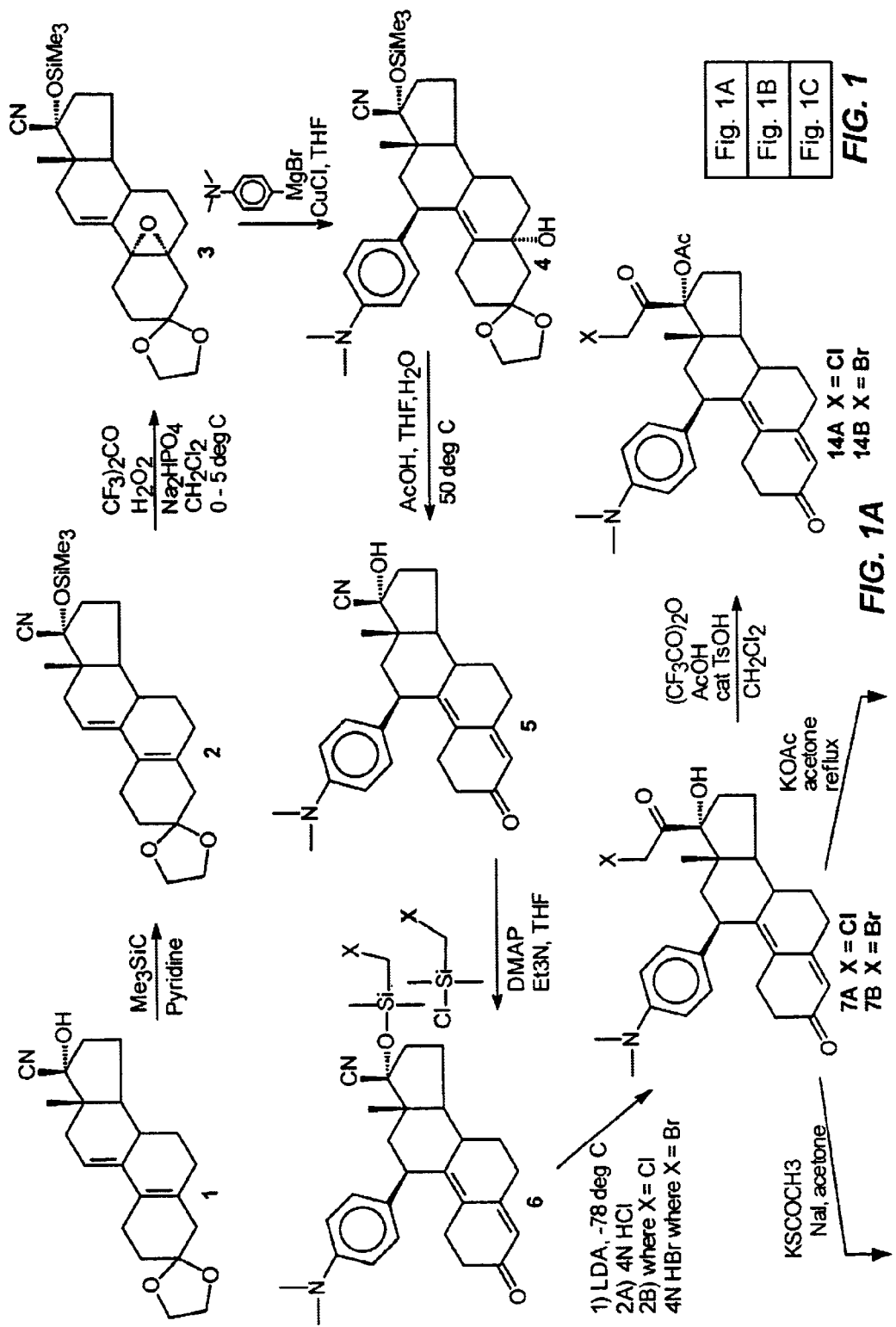
FIGS. 1 (1A, 1B and 1C) through 3 illustrate the synthetic schemes used to prepare the compounds of Formula I.

In one aspect, the present invention provides compounds having the general formula:

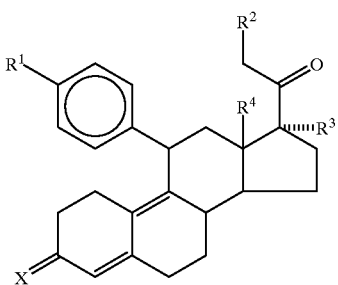

I

In Formula I, $R^1$ is a functional group including, but not limited to, —$OCH_3$, —$SCH_3$, —$N(CH_3)_2$, —$NHCH_3$, —CHO, —$COCH_3$ and —$CHOHCH_3$. $R^2$ is a functional group including, but not limited to, halogen, alkyl, acyl, hydroxy, alkoxy, acyloxy, alkyl carbonate, cypionyloxy, S-alkyl and S-acyl. $R^3$ is a functional group including, but not limited to, alkyl, hydroxy, alkoxy and acyloxy. $R^4$ is a functional group including, but not limited to, hydrogen and alkyl. Finally, X is a functional group including, but not limited to, =O and =N—$OR^5$, wherein $R^5$ is a member selected from the group consisting of hydrogen and alkyl.

The term "alkyl" is used herein to refer to a branched or unbranched, saturated or unsaturated, monovalent hydrocarbon radical having from 1–12 carbons and, preferably, from 1–6 carbons. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. As used herein, the term alkyl encompasses "substituted alkyls." Substituted alkyl refers to alkyl as just described including one or more functional groups such as lower alkyl, aryl, aralkyl, acyl, halogen (i.e., alkylhalos, e.g., $CF_3$), hydroxy (e.g., hydroxymethyl), amino, alkylamino, acylamino, acyloxy, alkoxy (e.g., methoxymethyl), mercapto and the like. These groups may be attached to any carbon atom of the lower alkyl moiety.

The term "alkoxy" is used herein to refer to the —OR group, where R is a lower alkyl, substituted lower alkyl, aryl, substituted aryl, aralkyl or substituted aralkyl. Suitable alkoxy radicals include, for example, methoxy, ethoxy, phenoxy, t-butoxy (e.g., methoxyethoxy, methoxymethoxy, etc.), etc.

The term "acyloxy" is used herein to refer to an organic radical derived from an organic acid by the removal of a hydrogen. The organic radical can be further substituted with one or more functional groups such as alkyl, aryl, aralkyl, acyl, halogen, amino, thiol, hydroxy, alkoxy, etc. An example of such a substituted organic radical is glycinate (e.g., —$OC(O)CH_2NH_2$). Suitable acyloxy groups include, for example, acetoxy, i.e., $CH_3COO$—, which is derived from acetic acid, formyloxy, i.e., H.CO.O—, which is derived from formic acid and cypionyloxy, which is derived from 3-cyclopentylpropionic acid.

The term "halogen" is used herein to refer to fluorine, bromine, chlorine and iodine atoms.

The term "hydroxy" is used herein to refer to the group —OH.

The term "acyl" denotes groups —C(O)R, where R is alkyl or substituted alkyl, aryl or substituted aryl as defined herein.

The term "aryl" is used herein to refer to an aromatic substituent which may be a single ring or multiple rings which are fused together, linked covalently, or linked to a common group such as an ethylene or methylene moiety. The aromatic ring(s) may include phenyl, naphthyl, biphenyl, diphenylmethyl, 2,2-diphenyl-1-ethyl, and may contain a heteroatom, such as thienyl, pyridyl and quinoxalyl. The aryl group may also be substituted with halogen atoms, or other groups such as nitro, carboxyl, alkoxy, phenoxy, and the like. Additionally, the aryl group may be attached to other moieties at any position on the aryl radical which would otherwise be occupied by a hydrogen atom (such as 2-pyridyl, 3-pyridyl and 4-pyridyl).

The term "alkyl carbonate" is used herein to refer to the group —OC(O)OR, where R is alkyl, substituted alkyl, aryl, or substituted aryl as defined herein.

The term "S-alkyl" is used herein to refer to the group —SR, where R is lower alkyl or substituted lower alkyl.

The term "S-acyl" is used herein to refer to a thioester derived from the reaction of a thiol group with an acylating agent. Suitable S-acyls include, for example, S-acetyl, S-propionyl and S-pivaloyl. Those of skill in the art will know that S-acyl refers to such thioesters regardless of their method of preparation.

The terms "N-oxime" and "N-alkyloxime" are used herein to refer to the group =N—$OR^5$, wherein $R^5$ is, for example, hydrogen (N-oxime) or alkyl (N-alkyloxime). Those of skill in the art will know that the oximes can consist of the syn-isomer, the anti-isomer or a mixture of both the syn- and anti-isomers.

Within Formula I, certain embodiments are preferred, namely those in which $R^1$ is —$N(CH_3)_2$; those in which $R^2$ is halogen or alkoxy; those in which $R^3$ is acyloxy; those in which $R^4$ is alkyl (e.g., methyl and ethyl); and those is which X is =O or =N—$OR^5$, wherein $R^5$ is hydrogen or alkyl. More particularly, compounds which are preferred are those in which $R^1$ is —$N(CH_3)_2$; $R^2$ is halogen; $R^3$ is acyloxy; and $R^4$ is alkyl. Within this embodiment, compounds which are particularly preferred are those in which $R^2$ is F, Br or Cl; and $R^4$ is methyl. Also preferred are compounds in which $R^1$ is —$N(CH_3)_2$; $R^2$ is alkyl; $R^3$ is acyloxy; $R^4$ is alkyl; and X is =O. Also preferred are compounds in which $R^1$ is —$N(CH_3)_2$; $R^2$ is alkoxy; $R^3$ is acyloxy; $R^4$ is alkyl; and X is =O. Within this embodiment, compounds which are particularly preferred are those in which $R^2$ is methoxy or ethoxy; and $R^3$ is acetoxy. Also preferred are compounds in which $R^1$ is —$N(CH_3)_2$; $R^2$ is hydroxy; $R^3$ is acyloxy; $R^4$ is alkyl; and X is =O. Also preferred are compounds in which $R^1$ is —$N(CH_3)_2$; $R^2$ and $R^3$ are both acyloxy; $R^4$ is alkyl; and X is =O. Within this embodiment, compounds which are particularly preferred are those in which $R^2$ and $R^3$ are both acetoxy. Also preferred are compounds in which $R^1$ is —$N(CH_3)_2$; $R^2$ is S-acyl; $R^3$ is hydroxy or acyloxy; $R^4$ is alkyl; and X is =O. Also preferred are compounds in which $R^1$ is —$N(CH_3)_2$; $R^2$ is cypionyloxy; $R^3$ is acetoxy; $R^4$ is alkyl; and X is =O. Also preferred are compounds in which $R^1$ is —$N(CH_3)_2$; $R^2$ is methoxy; $R^3$ is acetoxy; $R^4$ is alkyl; and X is =N—$OR^5$, wherein $R^5$ is, for example, hydrogen or alkyl (e.g., methyl, ethyl, etc.). Also preferred are compounds in which $R^1$ is —$N(CH_3)_2$; $R^2$ and $R^3$ are both acetoxy; $R^4$ is alkyl; and X is =N—$OR^5$, wherein $R^5$ is, for example, hydrogen or alkyl (e.g., methyl, ethyl, etc.).

Specific preferred compounds include, but are not limited to, 17α-acetoxy-21-fluoro-11β-(4-N,N-dimethylaminophenyl)-19-norpregna-4,9-diene-3,20-dione, 17α-acetoxy-21-chloro-11β-(4-N,N-dimethylaminophenyl)-19-norpregna-4,9-diene-3,20-dione, 17α-acetoxy-21-bromoro-11β-(4-N,N-dimethylawninophenyl)-19-norpregna-4,9-diene-3,20-dione, 17α,21-diacetoxy-11β-(4-N,N- dimethylaminophenyl)-19-norpregna-4,9-diene-3,20-dione, 17α-hydroxy-21-acetylthio-11β-(4-N,N-dimethylaminophenyl)-19-norpregna-4,9-diene-3,20-dione, 17α-acetoxy-21-acetylthio-11β-(4-N,N-dimethylaminophenyl)-19-norpregna-4,9-diene-3,20-dione, 17α-acetoxy-21-ethoxy-11β-(4-N,N-dimethylaminophenyl)-19-norpregna-4,9-diene-3,20-dione, 17α-acetoxy-21-methyl-11β-(4-N,N-dimethylamino-phenyl)-19-norpregna-4,9-diene-3,20-dione, 17α-acetoxy-21-methoxy-11β-(4-N,N-dimethylaminophenyl)-19-norpregna-4,9-diene-3,20-dione, 17α-acetoxy-21-ethoxy-11β-(4-N,N-dimethylaminophenyl)-19-norpregna-4,9-diene-3,20-dione, 17α-acetoxy-21-(3'-cyclopentylpropionyloxy)-11β-(4-N,N-dimethylaminophenyl)-19-norpregna-4,9-diene-3,20-dione, 17α-acetoxy-21-hydroxy-11β-(4-N,N-dimethylaminophenyl)-19-norpregna-4,9-diene-3,20-dione, 17α,21-diacetoxy-11β-(4-N,N-dimethylaminophenyl)-19-norpregna-4,9-diene-3,20-dione3-oxime, and 17α-acetoxy-21-methoxy-11β-(4-N,N-dimethylaminophenyl)-19-norpregna-4,9-diene-3,20-dione 3-oxime.

The compounds of the present invention can readily be synthesized in a variety of ways using conventional synthetic chemistry techniques. Typically, the compounds of the present invention are prepared using the synthetic schemes set forth in FIGS. 1, 2 and 3. Generally, a number of different functional groups, such as F, Cl, Br, Me, hydroxy, methoxy, ethoxy, acyloxy, cypionyloxy and acylthio, have been introduced at C-21 of lead compound 17-α-acetoxy-11β-(4-N,N-dimethylaminophenyl)-19-norpregna-4,9-diene-3,20-dione (CDB-2914 or C-21H) using the synthetic schemes set forth in FIGS. 1, 2 and 3. For instance, the Silicon Nucleophilic Annulation Process (SNAP) on 17β-cyanohydrin (5) was used to prepare all of the 21-halogenated compounds with the exception of the 21-fluoro compound. This compound, however, was readily obtained by reacting the 21-mesylate with KF in acetonitrile in the presence of a crown ether. In addition, the 17α-acetoxy-21-ol compound (41) was obtained selectively from the ethoxyethylidenedioxy derivative (18) by means of buffered hydrolysis, whereas the 17α-ol-21-acetate derivative (8) was prepared from reacting the 21-halo compound with KOAc. It is interesting to note that both the 21-acetate and the 17-acetate produced the 17α,21-diol (9) by a base catalyzed methanolosis. Thereafter, this 17α,21-diol was readily converted to the 17α,21-diacetate (15) by a mixed anhydride procedure. With regard to the synthesis of 17α-acetoxy-21-cypionate (40), the hydroxyl group at C-21 of the 17α,21-diol (9) was first converted to the corresponding cypionate (39) and then the 17α—OH group was acetylated. The 17α-acetoxy-21-thioacetate (17) was obtained by reaction of the 21-iodo compound generated in situ from the corresponding bromo compound (7B), with potassium thioacetate followed by acetylation of the 17α-alcohol as shown in the synthetic scheme set forth in FIG. 1.

Figure 2:
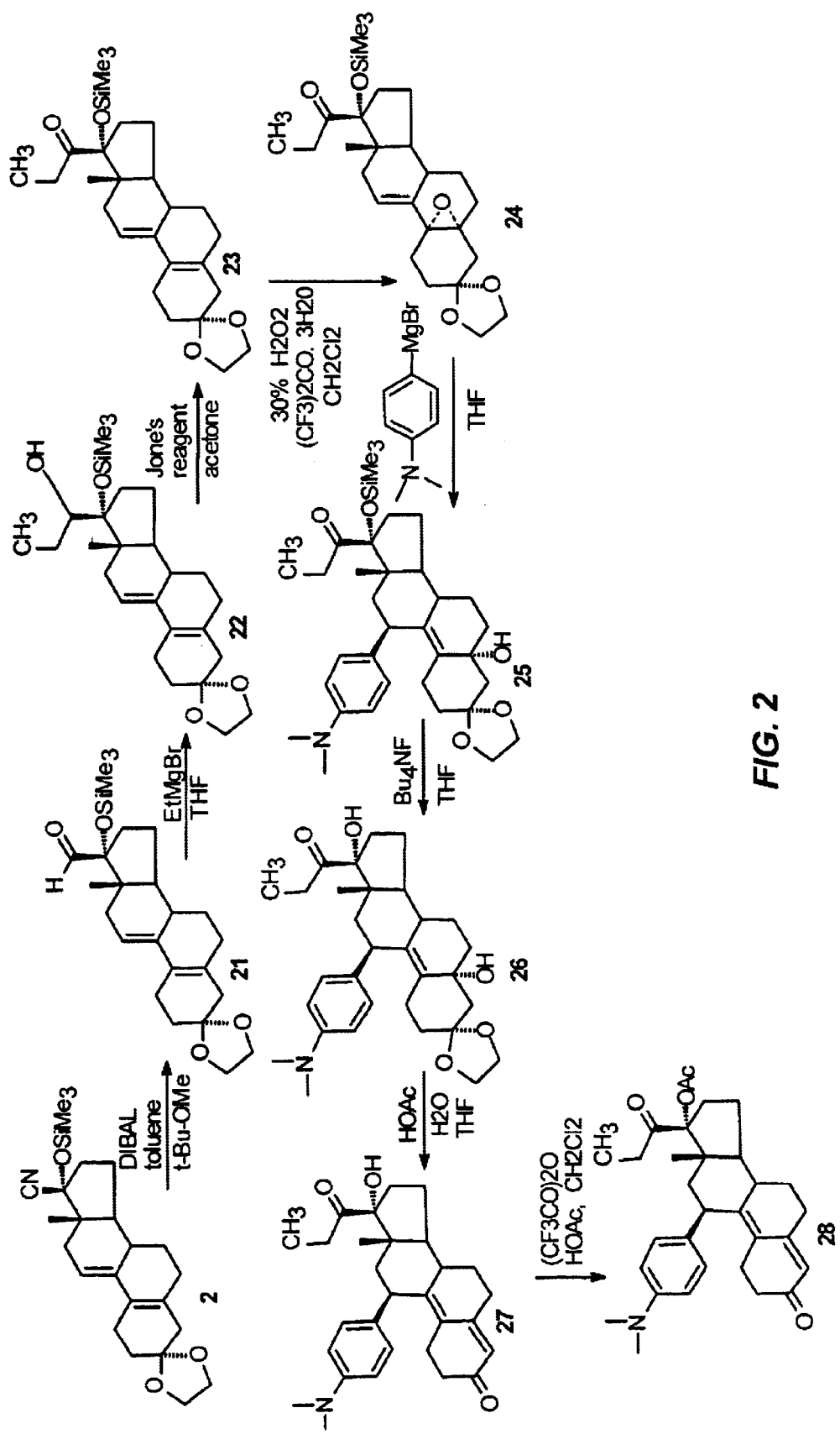

Moreover, the 21-methyl analog (28) was prepared following the synthetic route set forth in FIG. 2. The key reactions in this scheme are (1) the conversion of the 17β-cyanohydrin to the 17α-trimethylsilyloxy, 17β-aldehyde, and (2) the creation of the 21-methylprogesterone skeleton (21→22).

Figure 3:
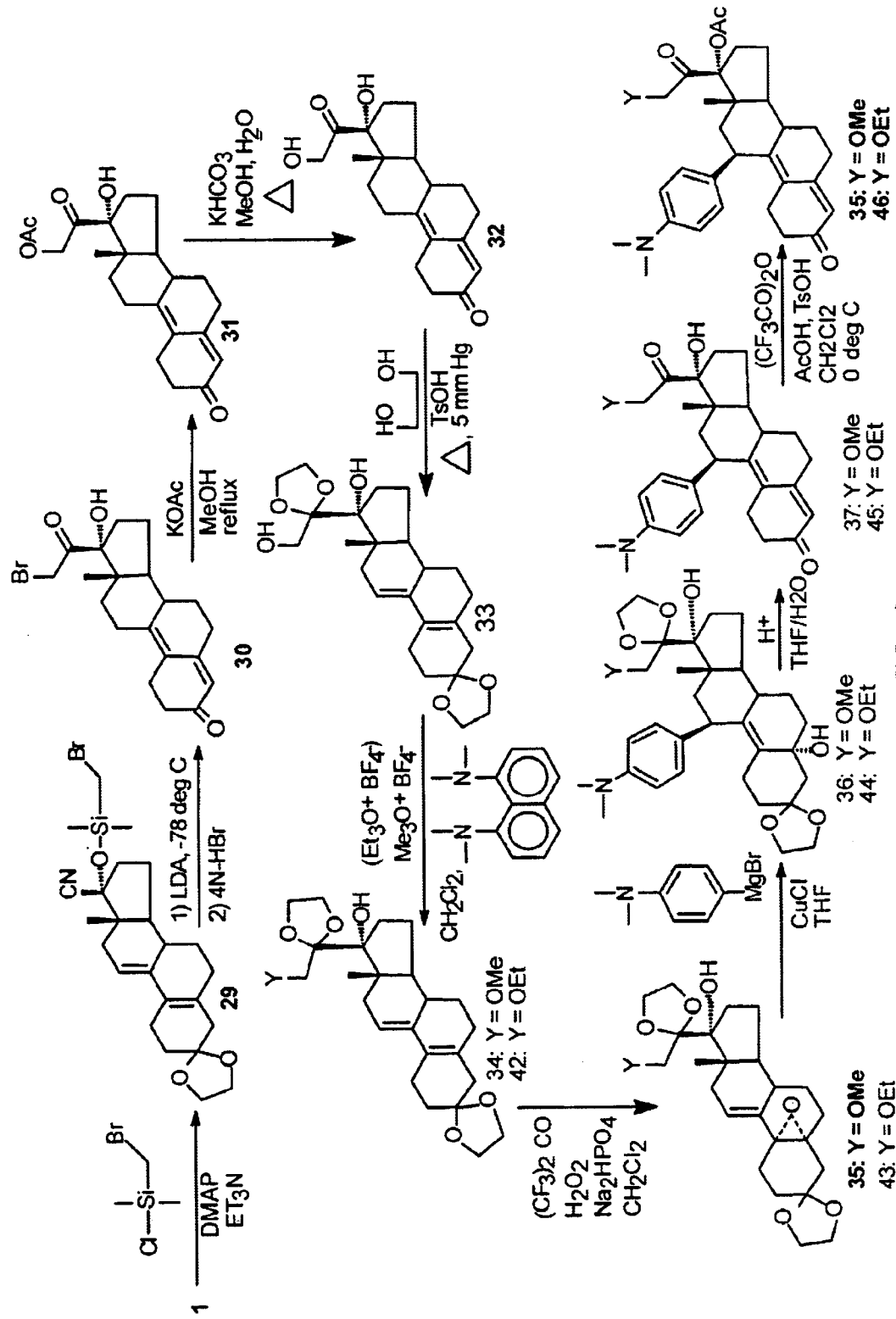

In addition, the 21-methoxy analog (38) was obtained following the synthetic scheme set forth in FIG. 3. The key step in this scheme is the reaction of the 17α,21-diol protected at C-3 and C-20 with Meerwein's trinethyloxonium tetrafluoroborate salt in the presence of the sterically more hindered, less nucleophilic base, 1,8-bis (dimethylamino)naphthalene, as the proton sponge to selectively methylate the less-hindered 21-hydroxyl group. The subsequent epoxidation of the crude 21-methoxy compound (34) produced a 2:1 mixture of α and β epoxides as evidenced by $^1$H NMR. The crude epoxide (35) was subjected directly to the copper (I) catalyzed conjugate Grignard addition, assuming 66% of the crude epoxide was the desired α epoxide, hydrolysis and acetylation gave the 21-methoxy compound (38) was a purity of 98%. Following similar procedures, the 21-ethoxy compound (46) was obtained using triethyloxonium tetrafluoroborate salt. Treatment of the 21-acetete (15) and 21-methoxy compound (38) with hydroxylamine HCl followed by adjustment of pH 7 provided the desired 3-oximes, 47 and 48, respectively, as a mixture of syn- and anti-isomers. Under these conditions, the sterically hindered C-20 ketone was intact as evidenced by IR spectroscopy. A more detailed description of the synthetic protocols used to prepare the compounds of the present invention is set forth hereinbelow in the example section.

Quite surprisingly, the compounds of Formula I possess potent antiprogestational activity with minimal antiglucocorticoid activity. As a result of their antiprogestational activity, the compounds of Formula I can advantageously be used, inter alia, to antagonize endogenous progesterone; to induce menses; to treat endometriosis; to treat dysmenorrhea; to treat endocrine hormone-dependent tumors; to treat uterine fibroids; to inhibit uterine endometrial proliferation; to induce labor; for hormone therapy; and for contraception.

More particularly, compounds having anti-progestational activity are characterized by antagonizing the effects of progesterone. As such, the compounds of the present invention are of particular value in the control of hormonal irregularities in the menstrual cycle, for controlling endometriosis and dysmenorrhea, and for inducing menses. In addition, the compounds of the present invention can be used as a method of providing hormone therapy either alone or in combination with estrogenic substances in postmenopausal women, or in women whose ovarian hormone production is otherwise compromised.

Moreover, the compounds of the present invention can be used for control of fertility during the whole of the reproductive cycle. For long-term contraception, the compounds of the present invention can be administered either continuously or periodically depending on the dose. In addition, the compounds of the present invention are of particular value as postcoital contraceptives, for rendering the uterus inimical to implantation; and as "once a month" contraceptive agents. They can be used in conjunction with prostaglandins, oxytocics and the like.

A further important utility for the compounds of the present invention lies in their ability to slow down growth of hormone-dependent cancers. Such cancers include kidney, breast, endometrial, ovarian cancers, and prostate cancer which are characterized by possessing progesterone receptors and can be expected to respond to the products of this invention. Other utilities of the compounds of the present invention include the treatment of fibrocystic disease of the breast and uterine.

Compounds suitable for use in the above method of the present invention can readily be identified using in vitro and in vivo screening assays known to and used by those of skill in the art. For instance, a given compound can readily be screened for its antiprogestational properties using, for example, the anti-McGinty test and/or the anti-Clauberg test described in the examples. In addition, a given compound can readily be screened for its ability to bind the progesterone and/or glucocorticoid receptors using the assays described in the examples. Moreover, a given compound can readily be screened for its ability to inhibit malignant tumor cell growth or to abolish tumorigenicity of malignant cells in vitro or in vivo. For instance, tumor cell lines can be exposed to varying concentrations of a compound of interest, and the viability of the cells can be measured at set time points using, for example, the alamar Blue® assay (commercially available from BioSource, International of Camarillo, Calif.). Other assays known to and used by those of skill in the art can be employed to identify compounds useful in the methods of the present invention.

The compounds according to the present invention can be administered to any warm-blooded mammal such as humans, domestic pets, and farm animals. Domestic pets include dogs, cats, etc. Farm animals include cows, horses, pigs, sheep goats, etc.

The amount of active ingredient that can be combined with a carrier material to produce a single dosage form will vary depending upon the disease treated, the mammalian species, and the particular mode of administration. For example, a unit dose of the steroid can preferably contain between 0.1 milligram and 1 gram of the active ingredient. A more preferred unit dose is between 0.001 and 0.5 grams. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the area.

The compounds of the present invention can be administered by a variety of methods. Thus, those products of the invention that are active by the oral route can be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. Products of the invention active on parenteral administration can be administered by depot injection, implants including Silastic™ and biodegradable implants, intramuscular and intravenous injections.

Compositions can be prepared according to any method known to the art for the manufacture of pharmaceutical compositions and such compositions can contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients can be, for example, inert diluents, such as calcium carbonate, sodium carbonate, lactose, calcium phosphate or sodium phosphate, granulating and disintegrating agents, such as maize starch, or alginic acid; binding agents, such as starch, gelatin or acacia; and lubricating agents, such as magnesium stearate, stearic acid and talc. Tablets can be uncoated or, alternatively, they can be coated by known methods to delay disintegration and adsorption in the gastrointestinal tract and thereby provide a sustained action over a longer period. For example, a time delay such as glyceryl monostearate or glyceryl distearate alone or with a wax can be employed.

Formulations for oral use can also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmolarity.

Oil suspensions can be formulated by suspending the active ingredient in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These compositions can be preserved by the addition of an antioxidant such as ascorbic acid.

Dispersible powders and granules of the invention suitable for preparation of an aqueous suspension by the addition of water can be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, can also be present.

The pharmaceutical compositions of the invention can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening and flavoring agents.

Syrups and elixirs can be formulated with sweetening agents, such as glycerol, sorbitol or sucrose. Such formulations can also contain a demulcent, a preservative, a flavoring or a coloring agent.

The pharmaceutical compositions of the invention can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent, such as a solution of 1,3-butanediol. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The compounds of this invention can also be administered in the form of suppositories for rectal administration of the drug. These compositions can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

They can also be administered by in intranasal, intraocular, intravaginal, and intrarectal routes including suppositories, insufflation, powders and aerosol formulations.

Products of the invention which are preferably administered by the topical route can be administered as applicator sticks, solutions, suspensions, emulsions, gels, creams, ointments, pastes, jellies, paints, powders, and aerosols.

The invention will be described in greater detail by way of specific examples. The following examples are offered for illustrative purposes, and are intended neither to limit or define the invention in any manner.

EXAMPLES

A. Preparation of the Compounds of Formula I

Example I

This example illustrates the preparation and properties of 17α-acetoxy-21-fluoro-11β-(4-N,N-dimethylaminophenyl)-19-norpregna-4,9-diene-3,20-dione(13) via the Silicon Nucleophilic Annulation Process (SNAP) of 5.

Step 1. 3,3-Ethylenedioxy-17β-cyano-17α-trimethylsilyloxyestra-5(10),9(11)-diene (2):

Under nitrogen, a solution of the cyanohydrin ketal (1, 15 g, 43.9 mmol) in pyridine (85 mL) was treated with chlorotrimethylsilane (28 mL=27.11 g, 221 mmol) and the mixture was stirred at room temperature for 5 hours. The reaction was monitored by Thin Layer Chromatography (TLC) in 2% acetone in $CH_2Cl_2$. The reaction mixture was poured into a 50:50 mixture of ice/saturated sodium bicarbonate solution (IL), stirred until the ice was melted, and extracted with hexanes (3×). The organic extracts were washed with water (2×), brine (1×), combined, dried over $Na_2SO_4$, and concentrated in vacuo. The remaining pyridine was azeotropically removed in vacuo with heptane to give 18 g of the crude product as a foam. Crystallization from ether/hexanes gave 16.35 g of the pure silyl ether (2) as a white solid in 90% yield; mp=100–102° C. FTIR (KBr, diffuse reflectance) $v_{max}$ 2880, 2232 and 1254 $cm^{-1}$. NMR ($CDCl_3$) δ 0.11 (s, 9H, $OSiMe_3$), 0.73(s, 3H, 18—$CH_3$), 3.83(s, 4H, —$OCH_2CH_2O$—) and 5.49 (br s, 1H, 11α-H).

Step 2. 3,3-Ethylenedioxy-5α,10α-epoxy-17β-cyano-17α-trimethylsilyloxyestra-9(11)-ene (3):

Hydrogen peroxide (30%, 6 mL, 58.6 mmol) was added to a vigorously stirred mixture of hexafluoroacetone trihydrate (11.8 g, 53.6 mmol) and $Na_2HPO_4$ (6.8 g, 47.9 mmol) in $CH_2Cl_2$ (150 mL) cooled to 0° C. in an ice bath. After stirring at 0° C. for 30 minutes, a solution of the silyl ether (2, 16 g, 38.7 mmol) in $CH_2Cl_2$ (10 mL), pre-cooled to 0° C. was added. The mixture was then stirred at 0° C. for 8 hr. At that time TLC in 5% acetone/$CH_2Cl_2$ indicated incomplete reaction and the mixture was then stirred overnight at 4° C. The reaction mixture was diluted with $CH_2Cl_2$ (200 mL) and washed with 10% sodium sulfite solution (2×), saturated sodium bicarbonate solution (1×) and brine (1×). The organic layers were combined, dried over $Na_2SO_4$, filtered and concentrated in vacuo to give 16.8 g of the crude epoxide mixture which consists of a 70:30 mixture of the 5α,10α-epoxide and 5β,10β-epoxide. Crystallization of the crude mixture from ether/hexanes afforded 8.5 g of the pure 5α,10α-epoxide (3) as a white solid in 51% yield; mp=164–165° C. FTIR (KBr, diffuse reflectance) $v_{max}$ 2940, 2872, 2228 and 1252 $cm^{-1}$. NMR ($CDCl_3$) δ 0.23 (s, 9H, $OSiMe_3$), 0.91 (s, 3H, 18-$CH_3$), 3.91 (s, 4H, $OCH_2CH_2O$) and 6.12 (br s, 1H, 11α-H).

Step 3. 3,3-Ethylenedioxy-5α-hydroxy-11β-4-N,N-dimethylaminophenyl)-17β-cyano-17α-trimethylsilyloxy-estr-9(10)-ene (4):

Magnesium (2.6 g, 107 mmol) was added to a 1.0 L, 3-neck flask equipped with a magnetic stir bar, addition funnel and a condenser. A crystal of iodine was added followed by dry THF (100 mL) and a few drops of 1,2-dibromoethane. The mixture was stirred under nitrogen and heated in a warm water bath until evidence of reaction was observed. A solution of 4-bromo-N,N-dimethylaniline (19.6 g, 98 mmol) in dry THF (100 mL) was then added dropwise over a period of 20 min. and the mixture stirred for an additional 1.5 hours. Solid copper (I) chloride (1 g, 10.1 mmol) was added followed 30 minutes later by a solution of the 5α,10α-epoxide (3, 8.4 g, 19.55 mmol) in dry TRF (10 mL). The mixture was stirred at room temperature for 1 hr., then quenched by the addition of saturated $NH_4Cl$ solution (100 mL). With vigorous stirring, air was drawn through the reaction mixture for 30 minutes. The mixture was diluted with ether (250 mL) and the layers allowed to separate. The THF/ether solution was washed with 10% $NH_4Cl$ solution (3×), 2 N $NH_4OH$ solution (3×) and brine (1×). The organic layers were combined, dried over $Na_2SO_4$, filtered and concentrated in vacuo to give the crude product. Crystallization of the crude product from ether gave 8.6 g of the pure product 4 as a white solid in 80% yield; mp=222–224° C. dec. FTIR KBr, diffuse reflectance) $v_{max}$ 3221, 2951, 2232, 1613, 1517 and 1253 $cm^{-1}$. NMR ($CDCl_3$) δ 0.20 (s, 9H, $OSiMe_3$), 0.5 (s, 3H, 18-$CH_3$), 2.83 (s, 6H $NMe_2$), 3.9 (m, 4H, $OCH_2CH_2O$), 4.3 (m, 1H, 11α-H), 6.63 (d, J=9 Hz, 2H, 3' and 5' aromatic CH) and 7.03 (d, J=9Hz, 2', and 6' aromatic CH).

Step 4. 11β-(4-N,N-Dimethylaminophenyl)-17β-cyano-17α-hydroxyestra-4,9-dien-3-one (5):

A solution of the Grignard adduct (4, 8.5 g, 15.4 mmol) was dissolved in THF (50 mL) and the system was flushed with nitrogen. Glacial acetic acid (150 mL) and water (50 mL) were added and the mixture was heated at 50° C. for 4 hrs. The volatile substances were removed in vacuo under a stream of nitrogen and the residual acid neutralized with $NH_4OH$. The mixture was extracted with $CH_2Cl_2$ (3×). The organic fractions were washed with water (2×), brine (1×), combined, dried over $Na_2SO_4$, filtered and concentrated in vacuo. Crystallization of the residue from ether gave 3.1 g of cyanohydrin (5) as a pale yellow solid. Chromatography of the mother liquors eluting with 50% EtOAc in hexanes followed by crystallization gave 1.8 g of an additional product. Total yield of the cyanohydrin 5, was 4.9 g in 76.2% yield; m.p.=152–154° C. FTIR (KBr, diffuse reflectance) $v_{max}$ 3384, 2950, 2231, 1646, 1606 and 1520 $cm^{-1}$. NMR ($CDCl_3$) δ 0.67 (s, 3H, 18-$CH_3$), 2.97 (s, 6H $NMe_2$), 4.38 (br s, 1H, 11α-H), 5.83 (s, 1H, 4-CH), 6.7 (d, J=9 Hz, 2H, 3' and 5' aromatic CH) and 7.1 (d, J=9 Hz, 2H, 2' and 6' aromatic CH).

Step 5. 11β-(4-N,N-Dimethylaminophenyl)-17β-cyano-17α-bromomethyldimethylsilyloxyestra-4,9-dien-3-one (6):

Under nitrogen, a solution of cyanohydrin (5) (4.8 g, 11.52 mmol), triethylamine (2.5 mL, 17.8 mmol) and dimethylaminopyridine (DMAP) (0.4 g, 3.3 mmol) in dry THF (50 mL) was treated with bromomethyldimethylsilyl chloride (2 mL, 14.66 mmol). The mixture was stirred overnight at room temperature, diluted with hexanes, filtered through Celite and concentrated in vacuo. Flash chromatography of the residue using 40% EtOAc in hexanes gave 4.8 g of the pure silyl ether (6) as a white solid in 73.4% yield; m.p.= 176–177° C. FTIR (KBr, diffuse reflectance) $v_{max}$ 2950, 2882, 2229, 1660, 1613 and 1519 cm$^{-1}$. NMR (CDCl$_3$) δ 0.41 (s, 6H, OSi(CH$_3$)$_2$), 0.6 (s, 3H, 18-CH$_3$), 2.61 (s, 2H, —SiCH$_2$Br), 2.91 (s, 6H, NMe$_2$), 4.4 (br m, 1H, 11-CH), 5.77 (s, 1H, 4-CH), 6.66 (d, J=9 Hz, 2H, 3' and 5' aromatic CH) and 7.05 (d, J=9 Hz, 2' and 6' aromatic CH).

Step 6A. 17α-Hydroxy-21-chloro- 11β-(4-N,N-dimethylaminophenyl)-19-norpregna-4,9-diene-3,20-dione (7A):

Under anhydrous conditions and using a mechanical stirrer, a solution of the silyl ether (6) (370 mg, 0.71 mmol) in dry THF (7.0 mL) was cooled to −78° C. and treated dropwise with a 1.5 M solution of lithium diisopropylamide in cyclohexane (1.2 mL, 1.77 mmol). The reaction mixture was stirred at −78° C. for 45 min. and then warmed to −40° C. The reaction was quenched by addition of 4 N HCl (10 mL) and allowed to warm to room temperature. The excess acid was neutralized with the cautious addition of saturated NaHCO$_3$ solution. The mixture was extracted with EtOAc. The organic extracts were washed with H$_2$O, and brine, combined, and dried over Na$_2$SO$_4$. Evaporation of the solvent gave 378 mg of the crude product. The material was chromatographed eluting with 7.5% acetone/CH$_2$Cl$_2$ to afford 179 mg of the 21-chloro ketone (7A) as a stable foam in 54% yield. MS (EI) m/z (relative intensity) 467 (M$^+$, 70), 431 (M$^+$ −36, 8), 134(18) and 121(100) FTIR (KBr, diffuse reflectance) $v_{max}$ 3363, 2940, 1727, 1641 and 1517 cm$^{-1}$. NMR (CDCl$_3$) δ 0.37 (s, 3H, 18-CH$_3$), 2.90 (s, 6H, NMe$_2$), 4.40 (br. d, 1H, 11α-H), 4.5 (dd., 2H, J=15 Hz, J'=12 Hz, 21-CH$_2$Cl), 5.77 (s, 1H, C-4 H), 6.67 and 7.0 (d, 4H, aromatic CH).

Generation of (7A) from (5): "One Pot" (Step 5 and 6) Chloromethyldimethyl-silylation/LDA Reaction:

A solution of cyanohydrin (5) (2.25 g, 5.4 mmol), TEA (1.02 mL, 7.29 mmol) and DMAP (165 mg, 1.35 mmol) in THF (20 mL) was treated with chloromethyl dimethylsilylchloride (0.82 mL, 6.21 mmol). The reaction was stirred overnight and diluted with THF (30 mL). The mixture was chilled to −78° C. and treated dropwise with LDA (1.5 M/C$_6$H$_{12}$, 14.4 mL). The mixture was stirred at −78° C. for 45 min. and then warmed to −40° C. The reaction was quenched by addition of 4N HCl and allowed to warm to room temperature. The excess acid was neutralized with saturated NaHCO$_3$ solution and diluted with water. The aqueous mixture was extracted with methylene chloride. The organic extracts were washed with H$_2$O, brine, combined and dried over Na$_2$SO$_4$. Evaporation of the solvent gave 3.24 g of the residue. The material was chromatographed eluting with 7.5% acetone/CH$_2$Cl$_2$) to afford 1.13 g of 7A in 45% yield, which was identical in all respects to the 21-chloroketone (7A) obtained from the previously described two step procedure.

Step 6B. 17α-Hydroxy-21-bromo-11β-(4-N,N-dimethylaminophenyl)-19-norpregna-4,9-diene-3,20-dione (7B):

Under anhydrous conditions and using a mechanical stirrer, a solution of the silyl ether 6 (2.9 g, 5.11 mmol) in dry THF (80 mL) was cooled to −78° C. and treated dropwise with a 1.5 M solution of lithium diisopropylamide (LDA) in cyclohexane (10.2 mL, 15.3 mmol). After 1 hr., the reaction mixture became very viscous, i.e., almost a gel. The reaction was quenched at −78° C. by addition of 4 N HBr (50 mL, 200 mmol) and the mixture allowed to warm to room temperature. The excess acid was neutralized by slow addition of concentrated NH$_4$OH solution (15 mL) and the mixture was poured into water (100 mL) and extracted with CH$_2$Cl$_2$ (3×). The organic extracts were washed with water (3×), combined, filtered through Na$_2$SO$_4$ and concentrated in vacuo to give 3.1 g of the crude product as a foam. Purification via Flash chromatography gave a 94:6 mixture of the 21-bromo-(7B) and 21-chloro-(7A) derivative evidenced by a reverse phase HPLC on a NovaPak column eluting with MeOH/H$_2$O/Et$_3$N (70:30:0.033) at a flow rate of 1.0 mL/min at λ=302 nm. MS(EI) m/z (relative intensity): 513 (M$^+$ +2, 10), 512 (M$^+$, 20), 431(18) and 121 (100). FTIR (KBr, diffuse reflectance) $v_{max}$ 3327, 2948, 1723, 1660, 1611 and 1518 cm$^{-1}$. NMR (CDCl$_3$) δ 0.3 (s, 3H, 18-CH$_3$), 2.80 (s, 6H, NMe$_2$), 4.3 (br m, 3H, 11α-H and 21-CH$_2$Br), 5.65 (s, 1H, 4-CH), 6.55 (d, J=9 Hz, 2H, 3' and 5' aroma (d, J=9 Hz, 2' and 6' aromatic CH). This mixture was used for the subsequent reaction without further purification.

Step 7. 17α-Hydroxy-21-acetoxy-11β-(4-N,N-dimethylaminophenyl)-19-norpregna-4,9-diene-3,20-dione (8):

Under nitrogen, a solution of a 94:6 mixture of the 21-halogenated steroid (7A and 7B (1.8 g, 3.5 mmol) and potassium acetate (10 g, 102 mmol) in acetone was refluxed for 2 hrs. At the end of that time, TLC (10% acetone/CH$_2$Cl$_2$) indicated no presence of starting material. The reaction mixture was cooled to room temperature, filtered, concentrated in vacuo, diluted with water (200 mL) and extracted with CH$_2$Cl$_2$ (3×). The organic extracts were washed with water (2×), combined, filtered through Na$_2$SO$_4$ and concentrated in vacuo to give 1.6 g of the crude acetate (8) as a foam in 93% yield. A small portion of the pure acetate (8) was solidified by trituration with ether for characterization. This solid did not have a proper melting point and remained a solid when heated to 300° C. MS (EI) m/z (relative intensity): 491(M$^+$, 72), 431(6), 314(17) and 121 (100) FTIR (KBr, diffuse reflectance) $v_{max}$ 3326, 2949, 1752, 1733, 1639, 1613, 1588 and 1519 cm$^{-1}$. NMR (CDCl$_3$) δ 0.43 (s, 3H, 18-CH$_3$), 2.27 (s, 3H, OAc), 3.0 (s, 6H, NMe$_2$), 4.5 (br. d., 1H, 11α-H), 5.25 (dd, J$_1$=29.7 Hz, J$_2$=24 Hz, 2H, CH$_2$OAc), 5.87 (s, 1H, 4-CH), 6.77 (d, J=9 Hz, 2H, 3' and 5'-aromatic CH) and 7.17 (d, J=8.7 Hz, 2H, 2' and 6'-aromatic CH). Anal. Calcd. for C$_{30}$H$_{37}$NO$_5$.½H$_2$O: C, 71.97; H, 7.65; N, 2.80; Found: C, 72.16; H, 7.48; N, 2.90

Step 8. 17α, 21-Dihydroxy-11β-(4-N,N-dimethylaminophenyl)-19-norpregna-4,9-diene-3,20-dione (9):

A solution of the 21-acetate (8) (1.6 g, 3.25 mmol) in MeOH (100 mL) was deoxygenated by bubbling through it a slow stream of nitrogen for 30 minutes. A similarly deoxygenated 0.5 M solution of KHCO$_3$ in deionized water (10 mL, 5 mmol) was added and the mixture heated to reflux under nitrogen and monitored by TLC (5% i-PrOH/CH$_2$Cl$_2$) which indicated a complete reaction after 2 hr. The mixture was neutralized with 1M AcOH solution and the methanol removed in vacuo under a stream of nitrogen. The residue was taken up in CH$_2$Cl$_2$ and washed with water (3×). The organic layers were combined, dried over Na$_2$SO$_4$, filtered and concentrated in vacuo to give 1.6 g of the residue. This material was purified by Flash chromatography using 3% i-PrOH/CH$_2$Cl$_2$) followed by precipitation from methanol with water to give 1.1 g of the diol (9) as a yellow amorphous solid in 75% yield; mp=softens at 130° C. FTIR (KBr, diffuse reflectance) $v_{max}$ 3391, 2946, 1712, 1654, 1612 and 1518 cm$^{-1}$. NMR (CDCl$_3$) δ 0.35 (s, 3H, 18-CH$_3$), 2.91 (s, 6H, NMe$_2$), 4.5 (m, 3H, 11α-H and C$\underline{H}_2$—OH), 5.77 (s, 1H, 4-CH), 6.67 (d, J=9 Hz, 2H, 3' and 5'-aromatic CH) and 7.0 (d, J=8.7 Hz, 2H, 2' and 6'-aromatic CH). MS (EI) m/z (relative intensity): 449(M$^+$, 51), 431(14), 419(9), 389 (27), 3432(9) and 121(100). Anal. Calcd. for C$_{28}$H$_{35}$NO$_4$.½H$_2$O: C, 73.33; H, 7.91; N, 3.05; Found: C, 73.52; H, 7.70; N, 3.06.

Step 9. 17α-Hydroxy-21-mesyloxy-11β-(4-N,N-Dimethylaminophenyl)-19-norpregna-4,9-diene-3,20-dione (10):

Under nitrogen, a solution of the diol (9) (0.5 g, 1.11 mmol) and triethylamine (0.25 mL, 1.8 mmol) in dry pyridine (10 mL) was cooled to 0° C. in an ice bath and treated with methanesulfonyl chloride (0.125 mL, 1.615 mmol). After stirring at 0° C. for 1 hr., TLC (10% acetone/CH$_2$Cl$_2$) of a quenched (EtOAc/H$_2$O) aliquot indicated complete reaction. Cold water (50 mL) was added and the mixture extracted with CH$_2$Cl$_2$ (3×). The organic layers were washed with water (3×), combined, dried over Na$_2$SO$_4$, filtered and concentrated in vacuo. Azeotropic in vacuo removal of trace pyridine using heptane gave 0.62 g of the residue. Purification via Flash chromatography using 10% acetone/CH$_2$Cl$_2$ followed by trituration with Et$_2$O gave 0.46 g of the pure 21-mesylate (10) as a yellow solid in 78.4% yield; m.p.= 146–149° C. FTIR (KBr, diffuse reflectance) $v_{max}$ 3298, 2947, 2738, 1630, 1614, 1518 and 1174 cm$^{-1}$. NMR (CDCl$_3$) δ 0.39 (s, 3H, 18-CH$_3$), 2.91 (s, 6H, NMe$_2$), 3.2 (s, 3H, OSO$_2$CH$_3$), 4.4 (br d, 1H, 11α-H), 5.27 (dd, J$_1$=27 Hz, J$_2$=18 Hz, 2H, CH$_2$OMs), 5.79 (s, 1H, 4-CH), 6.69 (d, J=9 Hz, 2H, 3' and 5'-aromatic CH) and 7.07 (d, J=9 Hz, 2H, 2' and 6'-aromatic CH).

Step 10. 17α-Hydroxy-21-fluoro-11β-(4-N,N-dimethylaminophenyl)-19-norpregna-4,9-diene-3,20-dione (11) and 17-Spirooxetano-3'-oxo-11β-(4-N,N-dimethylaminophenyl)-19-norpregna-4,9-dien-3-one (12):

Under nitrogen, a mixture of the 21-mesylate (10) (0.4 g, 0.758 mmol), potassium fluoride (0.5 g, 8.6 mmol) and 18-Crown-6 (0.5 g, 1.9 mmol) in anhydrous CH$_3$CN (15 mL) was heated to reflux and monitored by TLC (6% acetone/CH$_2$Cl$_2$) which indicated consumption of starting material and formation of two major products after 1 hr. The reaction mixture was cooled to room temperature, diluted with water (150 mL) and extracted with CH$_2$Cl$_2$ (3×). The organic extracts were washed with water (3×), combined, dried over Na$_2$SO$_4$, filtered and concentrated in vacuo. The mixture was separated via Flash chromatography using 6% acetone/CH$_2$Cl$_2$ to give 0.158 g of the 21-fluoro compound (11) as a pale yellow solid in 46% yield; m.p. 132–135° C. FTIR (KBr, diffuse reflectance) $v_{max}$ 3492–3303, 2948, 1733, 1652, 1610 and 1519 cm$^{-1}$. NMR (CDCl$_3$) δ 0.40 (s, 3H, 18-CH$_3$), 2.90 (s, 6H, NMe$_2$), 4.4 (br d, 1H, 11α-H), 5.26 (dd, J$_{HF}$=48.6 Hz, J$_1$=16.2 Hz, J$_2$=22 Hz, 2H, CH$_2$F), 5.77 (s, 1H, 4-CH), 6.67 (d, J=9 Hz, 2H, 3' and 5'-aromatic CH) and 7.01 (d, J=9 Hz, 2H, 2' and 6'-aromatic CH). MS(EI) m/z (relative intensity): 451 (M$^+$,33) and 121(100). In addition to the aforementioned compound 11, 0. 177 g of the oxetan-3'-one (12) was obtained as an off-white amorphous powder in 54.1% yield; m.p.=softens at 95° C. MS (EI): m/z (relative intensity) 431(M$^+$, 38), 134(14) and 121(100) FTIR (KBr, diffuse reflectance) $v_{max}$ 2941, 1809, 1663, 1613 and 1519 cm$^{-1}$. Analysis by a reverse phase HPLC on a NovaPak C$_{18}$ column eluting with CH$_3$CN/H$_2$O/Et$_3$N (50:50:0.033) at a flow rate of 1 mL/min and at λ=302 nm indicated this material to be of 97% purity whose retention time (R$_T$) is 13.39 min. NMR (CDCl$_3$) δ 0.55 (s, 3H, 18-CH$_3$), 2.91 (s, 6H, NMe$_2$), 4.45 (br d, J=6.7 Hz, 1H, 11α-H), 5.03 (dd, J$_1$=17.1 Hz, J$_2$=15.3 Hz, 2H, 21-CH$_2$), 5.79 (s, 1H, 4-CH), 6.69 (d, J=9 Hz, 2H, 3' and 5'-armonatic CH), 7.03 (d, J=9 Hz, 2H, 2' and 6'-aromatic CH). Anal. Calcd. for C$_{28}$H$_{33}$NO$_3$: C, 77.93; H, 7.71; N, 3.25; Found: C, 77.80; H, 7.62; N, 3.11.

Step 11. 17α-Acetoxy-21-fluoro-11β-(4-N,N-dimethylaminophenyl)-19-norpregna-4,9-diene-3,20-dione (13):

Under nitrogen, trifluoroacetic anhydride (1.75 mL, 12.39 mmol), glacial acetic acid (0.7 mL, 12.14 mmol) and dry CH$_2$Cl$_2$ (10 mL) were combined and stirred at room temperature for ½ hr. The mixture was cooled to 0° C. in an ice bath and toluenesulfonic acid monohydrate (0.1 g, 0.53 mmol) was added. A solution of the 21-fluoro-17α-alcohol (11) (0.28 g, 0.62 mmol) in dry CH$_2$Cl$_2$ was then introduced via syringe and the mixture stirred at 0° C. for 6.5 hrs. After that time, TLC (10% acetone/CH$_2$Cl$_2$) indicated a complete reaction. The mixture was diluted with water (3×), neutralized with concentrated NH$_4$OH solution and extracted with CH$_2$Cl$_2$ (3×). The organic extracts were washed with water (3×), combined, filtered through Na$_2$SO$_4$ and concentrated in vacuo to give 0.32 g of the crude product as a foam. Purification via Flash chromatography (5% acetone/CH$_2$Cl$_2$) followed by trituration with heptane and pentane gave 0.18 g of the pure 21-fluoro-17α-acetate (13) as a white amorphous solid in 58.8% yield; m.p. 169–173°. Analysis by a reverse phase HPLC on a NovaPak C18 column eluting with MeOH/H$_2$O/Et$_3$N (70:30:0.033) at a flow rate of 1 mL/min and at λ=302 nm indicated this material to be of 98.9% purity which has a retention time of R$_T$=5.97 min. MS(EI), m/z (relative intensity): 493(M$^+$, 32), 134 (14), 122(13) and 121(100). FTIR (KBr, diffuse reflectance) $v_{max}$ 2946, 1739, 1662, 1612 and 1510 cm$^{-1}$. NMR (CDCl$_3$) δ 0.40 (s, 3H, 18-CH $_3$), 2.10(s, 3H, OAc), 2.90 (s, 6H, NMe$_2$), 4.4 (br d, 1H, 11α-H), 4.95 (dq, J$_{HF}$=48 Hz, J$_1$=16 Hz, J$_2$=22 Hz, 2H, CH$_2$F), 5.80 (s, 1H, 4-CH), 6.67 (d, J=9 Hz, 2H, 3' and 5'-aromatic CH) and 7.03 (d, J=9 Hz, 2H, 2' and 6'-aromatic CH). Anal. Calcd. for C$_{30}$H$_{36}$FNO$_4$: C, 73.00; H, 7.35; N, 2.84; Found: C, 72.96; H, 7.47; N, 2.84.

Example II

This example illustrates the preparation and properties of 17α-acetoxy-21-chloro-11β-(4-N,N-dimethylaminophenyl)-19-norpregna-4,9-diene-3,20-dione (14A).

A solution of trifluoroacetic anhydride (2.2 mL, 15.56 mmol) in CH$_2$Cl$_2$ (25 mL) was treated with acetic acid (0.89 mL, 15.56 mmol). The mixture was stirred at room temperature for 30 min. and p-toluenesulfonic acid (137 mg, 0.72 mmol) was added. The mixture was chilled to 0° C. and a solution of 7A (364 mg, 0.78 mmol) in CH$_2$Cl$_2$ (2.0 mL) was added. The mixture was stirred for 2 hrs. and quenched with cautious addition of saturated NaHCO$_3$ solution. The mixture was extracted with CH$_2$Cl$_2$. The organic extracts were washed with H$_2$O and brine, combined and dried over Na$_2$SO$_4$. Evaporation of the solvent gave 412 mg of a stable foam. The material was chromatographed eluting with 5% acetone in $CH_2Cl_2$ to afford 210 mg of 8 in 53% yield as an amorphous foam which persisted recrystallization from a variety of solvents. Analysis by a reverse phase HPLC on a NovaPak $C_{18}$ column, eluting with 30% aq. MeOH with 0.033% TEA at a flow rate of 1.0 mL/min at $\lambda=260$ nm showed the material to be approximately 95% pure. Therefore, the material was purified by preparative HPLC on a Whatman Magnum Partisil 10-ODS-3 column eluting with aqueous MeOH with 0.033% TEA at a flow rate of 10 mL per minute at $\lambda=325$ nm to afford 158 mg of 14A as an amorphous yellow foam in 48% yield. FTIR (KBr, diffuse reflectance) $v_{max}$ 2947, 1731, 1660, 1610 and 1518 $cm^{-1}$. NMR ($CDCl_3$) δ 0.40 (s, 3H, 18-$CH_3$), 2.13 (s, 3H, 17α-OAc), 2.90 (s, 6H, N($CH_3$)$_2$), 4.23 (dd, J=15 Hz, J'=9 Hz, 2H, —$CH_2Cl$), 4.4 (br d, 1H, 11α-H), 5.72 (s, 1H, C-4H), 6.67 and 7.0 (d, 4H, aromatic CH). MS (EI) m/z (relative intensity): 510($M^+$, 6), 509 ($M^+$ −1, 16), 134 and 121(100). Anal. calcd. for $C_{30}H_{36}NO_4Cl$: C, 70.64; H, 7.11; N, 2.75; Found: C, 70.46; H, 7.10; N, 2.76.

Example III

This example illustrates the preparation and properties of 17α-acetoxy-21-bromo-11β-(4-N,N-dimethylaminophenyl)-19-norpregna-4,9-diene-3,20-dione (14B).

Step 1. Purification of 7B

The pure 21-bromo compound (7B) was isolated from a 90:10 mixture of the 21-halo product (7B:7A) by means of Waters Prep LC system on a NovaPak $C_{18}$ column (40×100 mm) eluting with 30% aq. MeOH and 0.03% $Et_3N$ at a flow rate of 35 mL/min and at $\lambda=334$ run. A total amount of 0.75 g of a 90:10 mixture (7B:7A) was chromatographed in 10 runs of 75 mg each to give of 0.5 g of the pure 21-bromo compound (7B) as a pale yellow solid in 67% yield. This material was >99% pure by analytical HPLC. FTIR (KBr, diffuse reflectance) $v_{max}$ 3327, 2948, 1723, 1660, 1611 and 1518 $cm^{-1}$. NMR ($CDCl_3$) δ 0.3 (s, 3H, 18-$CH_3$), 2.80 (s, 6H, $NMe_2$), 4.33 (dd, $J_1$=12 Hz, $J_2$=9 Hz, 2H, 21-$CH_2Br$), 4.40 (br d, 1H, 11α-H), 5.65 (s, 1H, 4-CH), 6.55 (d, J=9 Hz, 2H, 3' and 5' aromatic CH), 6.9 (d, J=9 Hz, 2' and 6' aromatic CH).

Step 2. Preparation of the Target Compound (14B)

Under nitrogen, a mixture of trifluoroacetic anhydride (1.64 mL, 11.68 mmol), glacial acetic acid (0.67 mL, 11.62 mmol) and dry $CH_2Cl_2$ (10 mL) was stirred at room temperature for 30 min and then cooled to 0° C. in an ice bath. p-Toluenesulfonic acid monohydrate (0.1 g, 0.52 mmol) was added followed by a solution of the 21-bromo alcohol (7B) (0.3 g, 0.59 mmol) in dry $CH_2Cl_2$ (2 mL). The reaction mixture was stirred at 0° C. and monitored by TLC (10% acetone/$CH_2Cl_2$) which indicated a complete reaction in two hrs. The mixture was diluted with water (10 mL), neutralized with concentrated $NH_4OH$ solution and extracted with $CH_2Cl_2$ (3×). The organic extracts were washed with $H_2O$ (3×), combined, filtered through $Na_2SO_4$ and concentrated in vacuo to give 0.35 g of the residue as a foam. This material was purified by Flash chromatography using 5% acetone/$CH_2Cl_2$ followed by crystallization from $Et_2O$/hexanes to give 0.24 g of the 21-bromo acetate (14B). Analysis by NMR indicated a significant amount of ether as solvent of crystallization. This material was then dissolved in $CH_2Cl_2$ (3 mL) and the solvent blown down to give an oil. Trituration with heptane followed by washing with pentane and drying in vacuo gave 0.16 g of the pure 21-bromo compound (14B) as a white crystalline solid in 49% yield: mp=141–145° C. MS (EI) m/z (relative intensity): 555 ($M^+$ +2, 82), 553 ($M^+$, 76), 475(13), 414(8), 372(13), 134(15) and 121(100). FTIR (KBr, diffuse reflectance) $v_{max}$ 2933, 1730, 1664, 1613, 1596 and 1519 $cm^{-1}$. NMR ($CDCl_3$) δ 0.40 (s, 3H, 18-$CH_3$), 2.13 (s, 3H, OAc), 2.80 (s, 6H, $NMe_2$), 4.07 (dd, $J_1$=14 Hz, $J_2$=7 Hz, 2H, 21-$CH_2Br$), 4.40 (br d, 1H, 11α-H), 5.83 (s, 1H, 4-CH), 6.67 (d, J=9 Hz, 2H, 3' and 5' aromatic CH), 7.07 (d, J=9 Hz, 2H, 2' and 6' aromatic CH). Anal. Calcd. for $C_{30}H_{36}BrNO_4 \cdot 1.5H_2O$: C, 64.98; H, 6.54; Br, 14.41; N, 2.53; Found: C, 64.82; H, 6.62; N, 2.27.

Example IV

This example illustrates the preparation and properties of 17α,21-diacetoxy-11α-(4-N,N-dimethylaminophenyl)-19-norpregna-4,9-diene-3,20-dione (15).

Under nitrogen, a mixture of trifluoroacetic anhydride (4.0 mL, 28.3 mmol), glacial acetic acid (1.6 mL, 27.7 mmol) and dry $CH_2Cl_2$ (10 mL) was stirred at room temperature for 30 min. and then cooled to 0° C. in an ice bath. p-Toluenesulfonic acid monohydrate (0.1 g, 0.53 mmol) was added followed by a solution of the 17α,21-diol (9, 0.345 g, 0.77 mmol) in dry $CH_2Cl_2$ (2 mL). The reaction mixture was stirred at 0° C. and monitored by TLC (10% acetone/$CH_2Cl_2$) which indicated a complete reaction in two hrs. The mixture was diluted with $H_2O$ (10 mL), neutralized with concentrated $NH_4OH$ solution and extracted with $CH_2Cl_2$ (3×). The organic layers were washed with $H_2O$ (3×), combined, filtered through $Na_2SO_4$ and concentrated in vacuo to give 0.4 g of the residue as a foam. This material was purified by Flash chromatography using 5% acetone/$CH_2Cl_2$ followed by trituration with heptane and pentane to give 0.24 g of the 17α,21-diacetate (15) as a yellow amorphous solid in 58.4% yield: mp=128–134° C. Analysis by a reverse phase HPLC on a NovaPak $C_{18}$ column eluting with $CH_3CN:H_2O:Et_3N$ (1:1:0.033) at a flow rate of 1 mL/min and at $\lambda=302$ nm indicated 15 to be of >98% purity which has a retention time of 12 min. MS (EI) m/z (relative intensity): 533 ($M^+$, 24), 134 (14), 122 (11) and 121(100). FTIR (KBr, diffuse reflectance) $v_{max}$ 2942, 1738.1663, 1611, 1518 and 1233 $cm^{-1}$. NMR ($CDCl_3$) δ 0.33 (s, 3H, 18-$CH_3$), 2.10 (s, 3H, OAc), 2.13(s, 3H, OAc), 2.90 (s, 6H, $NMe_2$), 4.43 (br d, 1H, 11α-H), 4.84 (dd, $J_1$=29.7 Hz, $J_2$=18 Hz, 2H 21-$CH_2Br$), 5.80 (s, 1H, 4-CH), 6.67 (d, J=9 Hz, 2H, 3' and 5' aromatic CH), 7.05 (d, J=9 Hz, 2H, 2' and 6' aromatic CH). Anal. Calcd. for $C_{32}H_{39}NO6 \cdot \frac{1}{3} H_2O$: C, 71.22; H, 7.41; N, 2.60; Found: C, 71.27; H, 7.35; N, 2.61.

Example V

This example illustrates the preparation and properties of 17α-acetoxy-21-acetylthio-11β-(4-N,N-dimethylaminophenyl)-19-norpregna-4,9-diene-3,20-dione (17).

Step 1. 17α-Hydroxy-21-acetylthio-11β-(4-N,N-dimethylaminophenyl)-19-norpregna-4,9-diene-3,20-dione (16):

The 17α-Hydroxy- 21-bromo compound (7B) (2.79 g, 5.44 mmol) dissolved in acetone (150 mL) was refluxed with sodium iodide (8.16 g, 54.4 mmol) for 1 hr in an atmosphere of nitrogen and then filtered directly into a suspension of potassium thioacetate (6.2 g, 54.4 mmol) in acetone (150 mL). After refluxing for an additional 2.5 hrs, the reaction mixture was cooled to room temperature, filtered, concentrated in vacuo, diluted with $H_2O$ and extracted with $CH_2Cl_2$. The organic fractions were washed with $H_2O$ and brine, combined and dried over sodium sulfate. The filtrate was evaporated and the residue was purified via flash silica gel column (6% acetone/$CH_2Cl_2$) to afford 1.99 g of 16 as a yellow foam in 72.1% yield. Crystallization of the foam from EtOAc/hexanes gave yellow crystals with m.p. 197–198° C. FTIR (KBr, diffuse reflectance) $v_{max}$ 3483, 2943, 1722, 1696, 1642, 1615, 1585 and 1520 cm$^{-1}$. NMR (CDCl$_3$) δ 0.40 (s, 3H, 18-CH$_3$), 2.41 (s, 3H, Ac), 2.95 (s, 6H, NMe$_2$), 3.32 (s, 1H, 17α-OH), 3.65 and 4.31 (AB-System, J=16.5 Hz, 2H, 21-CH$_2$), 4.36 (br d, 1H, 11α-H), 5.73 (s, 1H, 4-CH), 6.66 (d, J=9 Hz, 2H, 3' and 5'-aromatic CH) and 7.07 (d, J=9 Hz, 2H, 2' and 6'-aromatic CH). MS(EI) m/z (relative intensity): 507 (M$^+$). Anal. Calcd. for C$_{30}$H$_{37}$O$_4$NS: C, 70.79; H, 7.35; N, 2.76; S, 6.31; Found: C, 70.97; H, 2.75; N, 2.76; S, 6.29.

Step 2. Preparation of the Target Compound (17):

Under nitrogen, trifluoroacetic anhydride (8.5 mL, 61.95 mmol), glacial acetic acid (3.5 mL, 60.7 mmol) and dry CH$_2$Cl$_2$ (100 mL) were combined and stirred at room temperature for 20 min. The mixture was cooled to 0° C. in an ice bath and p-toluenesulfonic acid monohydrate (0.5 g, 2.65 mmol) was added. A solution of the 17-alcohol (16) (1.99 g, 3.99 mmol) in dry CH$_2$Cl$_2$ was added and the mixture stirred at 0–5° C. for 10 hr. The mixture was neutralized with saturated NaHCO$_3$ solution and extracted with CH$_2$Cl$_2$ (3×). The organic fractions were washed with H$_2$O (3×), combined and dried over Na$_2$SO$_4$. The filtrate was evaporated and the residue was purified via flash silica gel column (4.6% acetone/CH$_2$Cl$_2$) to afford 1.73 g of 17 as a yellow foam in 80.4% yield: m.p.=123–124° C. MS(EI) m/z (relative intensity): 549 (M$^+$). FTIR (KBr, diffuse reflectance) $v_{max}$ 2946, 1736, 1692, 1663, 1611 and 1518 cm$^{-1}$. NMR (CDCl$_3$) δ 0.39 (s, 3H, 18-CH$_3$), 2.18 (s, 3H, OAc), 2.38 (s, 3H, SAc), 2.92 (s, 6H, NMe$_2$), 3.91 (s, 2H, 21-CH2), 4.44 (br d, 1H, 11α-H), 5.78 (s, 1H, 4-CH), 6.67 (d, J=9 Hz, 2H, 3' and 5'-aromatic CH) and 7.08 (d, J=9 Hz, 2H, 2' and 6'-aromatic CH). Anal. Calcd for C$_{32}$H$_{39}$NO$_5$S: C, 69.92; H, 7.15; N, 2.55; S, 5.83; Found: C, 69.66; H, 7.12; N, 2.58; S, 5.59.

Example VI

This example illustrates the preparation and properties of 17α-acetoxy-21-methyl-11β-(4-N,N-dimethylaminophenyl)-19-norpregna-4,9-diene-3,20-dione (28):

Step 1. 3,3-Ethylenedioxy-17α-trimethylsilyloxyestra-5(10),9(11)-dien-17β-aldehyde (21).

The cyano trimethylsilyl ether (2) (16 g, 38.7 mmol) was dissolved in THF (30 mL, distilled from Lithium Aluminum Hydride (LAH)) in oven-dried glassware, and t-butyl methyl ether (300 mL) was added. The mixture was cooled to 0° C. in an ice bath. Diisobutylaluminum hydride (DIBAL-H) (75 mL, 1 M in toluene) was added to the mixture over 30 min. using an addition funnel. The reaction mixture was stirred under nitrogen at room temperature and monitored by HPLC (on a NovaPak C$_{18}$ column eluting with CH$_3$CN/H$_2$O/75:25). The reaction was complete after 4 hr. It was cooled to 0° C. in an ice bath and aq. acetic acid (40 mL, 50% ) was added. The mixture was diluted with H$_2$O and extracted with ether (3×). The ether extracts were washed with 10% acetic acid, H$_2$O, saturated NaHCO$_3$ solution, H$_2$O and brine. The combined organic layers were dried over Na$_2$SO$_4$ and concentrated in vacuo to yield 15.11 g of the crude aldehyde (21). Flash chromatography using 1% TH/CH$_2$Cl$_2$ gave 10.6 g of the pure product as a white solid in 65% yield; mp=105–109° C. MS(EI) m/z (relative intensity): 416 (M$^+$, 30), 270(47), 169 (44), 129 (47), 99(73), 86(31) and 73 (100). FTIR (KBr, diffuse reflectance) $v_{max}$ 2910 and 1731 cm$^{-1}$. NMR (CDCl$_3$) δ 0.11 (s, 9H, Si(CH$_3$)$_3$); 0.67 (s, 3H, 18-CH$_3$), 3.98 (s, 4H, OCH$_2$CH$_2$O), 5.60 (br s, 1H, C-11H) and 9.67 (s, 1H, 17β-CHO). Anal. Calcd. for C$_{24}$H$_{36}$O$_4$Si.⅙ hexane (C$_6$H$_{14}$): C, 69.67; H, 8.60; Found: C, 69.07; H, 8.79.

Step 2. 3,3-Ethylenedioxy-17α-trimethylsilyloxy-20ξ-hydroxy-21-methyl-19-norpregna-5(10),9(11)-diene (22).

In oven-dried glassware, the crude aldehyde (21) (30.35 g, 72.8 mmol) was dissolved in THF (432 mL, distilled from LAH) and cooled to 0° C. under nitrogen. Ethyl magnesium bromide (37 mL, 3 M in ether) was transferred via double-tipped needles to an additional funnel and then slowly added to the reaction mixture. The mixture was stirred at room temperature and monitored by TLC (2% acetone/CH$_2$Cl$_2$). Reaction was complete in 3 hr, so mixture was cooled to 0° C. and saturated NH$_4$Cl solution (310 mL) was added slowly. THF was evaporated in vacuo. The mixture was extracted with ether (3×) and brine, and dried over Na$_2$SO$_4$. The solvent was evaporated, yielding 31.03 g of the crude 20-hydroxy product (22) as a foam in 95% yield. This material was directly used without further purification in the subsequent reaction. FTIR (KBr, diffuse reflectance) $v_{max}$ 3503 and 2951 cm$^{-1}$. NMR (CDCl$_3$) δ 0.16 (s, 9H, Si(CH$_3$)$_3$), 0.75, 0.78 (2s, C-18 CH$_3$ for 20-α and 20-β isomers), 1.01 (t, J=6 Hz, 3H, C-21 CH$_3$), 3.98 (s, 4H, 3-OCH$_2$CH$_2$O—) and 5.60 (br s, 1H, 11α-H). MS (EI) m/z (relative-intensity): 447(M$^+$, 4.2), 418(17), 387(32), 356 (70) and 297 (100).

Step 3. 3,3-Ethylenedioxy-17α-trimethylsilyloxy-21-methyl-19-norpregna-5(10), 9(11)-dien-20-one (23):

The C-20 alcohol (22) (25.34 g, 56.7 mmol) was dissolved in acetone and stirred at 0° C. in an ice bath. Jone's reagent (42 mL) was added slowly to the above solution until the reaction mixture remained an orange color. Then isopropanol was added until the green color persisted. Ice H$_2$O (2 L) was added and stirred well. The mixture was extracted with EtOAc (3×), washed with H$_2$O (2×), saturated NaHCO$_3$, H$_2$O and brine. The combined organic layers were dried over Na$_2$SO$_4$ and concentrated in vacuo to give 18.83 g of the crude ketone (23). Flash chromatography using 1% ether/CH$_2$Cl$_2$ gave 7.3 g of the purified product as a foam in 29% yield. NMR (CDCl$_3$) δ 0.10 (s, 9H, Si(CH$_3$)$_3$), 0.51 (s, 3H, C-18 CH$_3$), 1.04 (t, J=7 Hz, 3H, C-21CH$_3$), 3.99 (s, 4 H, C-3 ketal) and 5.61 (br s, 1H, 11α-H).

Step 4. 3,3-Ethylenedioxy-5α,10α-epoxy-17α-trimethylsilyloxy-21-methyl-19-norpregna-9(11)-en-20-one (24):

Hexafluoroacetone trihydrate (2.20 g, 10 mmol) and CH$_2$Cl$_2$ (23 mL) were stirred vigorously under nitrogen in an ice bath. Solid Na$_2$HPO$_4$ (0.78 g, 6.5 mmol) was added. 30% Hydrogen peroxide (1.50 mL) was poured into the mixture. It was stirred 30 min. A chilled solution of the C-20 ketone (23) (3.00 g, 6.75 mmol) in CH$_2$Cl$_2$ (23 mL) was added slowly with a pipette. The reaction mixture was stirred overnight in the cold room at 4° C. TLC (2% acetone/CH$_2$Cl$_2$) showed reaction complete in the morning. CH$_2$Cl$_2$ was added to the reaction mixture and it was washed with Na$_2$SO$_3$ (2×), saturated NaHCO$_3$, and brine. Organic extracts were dried over Na$_2$SO$_4$ and concentrated to give 2.98 g of a 77:25 mixture of the crude α: β-epoxide (24) according to NMR in 95% yield. This mixture was directly used in the subsequent reaction without further purification. NMR (CDCl$_3$) δ 0.10 (s, 9H, Si(CH$_3$)$_3$), 0.51 (s, 3H, C-18 CH$_3$), 1.05 (t, J=6 Hz, 3H, C-21 CH$_3$), 3.94 (s, 4H, 3-OCH$_2$CH$_2$O—), 5.90 (br s, 1H, 11α-H for β-epoxide) and 6.09 (br s, 1H, 11α-H for α-epoxide).

Step 5. 3,3-Ethylenedioxy-5α-hydroxy-11β-(4-N,N-dimethylaminophenyl)-17α-trimethylsilyloxy-21-methyl-19-norpregn-9(10)-en-20-one (25):

Mg (2.80 g, 116.2 mmol), which was washed with 0.1 N HCl, then $H_2O$ and acetone and dried in vacuo, was weighed into dry round-bottomed flask equipped with a reflux condenser. A small crystal of iodine was added and the system was flushed with nitrogen and flame-dried. The flask was cooled to room temperature and 68.5 mL of THF distilled from LAH was added via syringe. 1,2-Dibromoethane (approx. 0.5 mL) was added and the mixture was stirred at room temperature. After bubbling began and the color of $I_2$ disappeared, a solution of 4-bromo-N,N-dimethylaniline (20.43 g, 102.1 mmol) in THF (34 mL) was added via syringe. The mixture was stirred until most the Mg had reacted. Copper (I) chloride (1.13 g, 114.2 mmol) was added as a solid and stirred for 20 min. The crude epoxide (24) (7.33 g, 15.91 mmol) in THF (49 mL) was then added using a syringe. The reaction mixture was stirred at room temperature for 30 min, at which time the reaction was complete by TLC (2% acetone/$CH_2Cl_2$). Saturated $NH_4Cl$ solution (25 mL) was added and stirred for 30 min while air was pulled through by slight vacuum. The mixture was diluted with $H_2O$, extracted with $CH_2Cl_2$ (3×), washed with $H_2O$ (2×) and brine, dried over $Na_2SO_4$, and evaporated under reduced pressure. The residue was purified by flash chromatography using 3% acetone/$CH_2Cl_2$) to afford 4.27 g of the pure product (25) in 46.1% yield. IR (KBr, diffuse reflectance) $v_{max}$ 3531, 2940, 1708, 1614, and 1518 $cm^{-1}$. NMR ($CDCl_3$) δ 0.09 (s, 9H, Si($CH_3$)$_3$), 0.19 (s, 3H, C-18 $CH_3$), 1.02 (t, J=7 Hz, 3H. C-12 $CH_3$), 2.88 (s, 6H, N($CH_3$)$_2$), 3.99 (m, 4H, $_3$—$OCH_2CH_2O$—), 4.26 (br d, 1H, 11α-H), 6.85 (dd, J=41 Hz, J'=10 Hz, 4H, aromatic CH). MS (EI) m/z (relative intensity): 581 ($M^+$, 46), 563(34), 391(37), 134(65) and 121(100).

Step 6. 3,3-Ethylenedioxy-5α,17α-dihydroxy-11β-(4-N,N-dimethylaminophenyl)-21-methyl-19-norpregn-9(10)-en-20-one (26):

Tetrabutylammonium fluoride (18.1 mL, 1 M in THF) was stirred with molecular sieves under nitrogen for approx. 1 hr. The 17α-trimethylsilyloxy compound (25) (3.50 g, 6.0 mmol) in THF (21 mL) which was distilled from LAH, was added to the mixture and stirred at room temperature for 1 hr. $H_2O$ was added and the THF was removed in vacuo. EtOAc was added to the mixture and was filtered through Celite. The product was extracted with EtOAc, washed with $H_2O$ and brine, and dried over $Na_2SO_4$. Evaporation of the solvent gave 3.19 g of the crude 5α,17α-dihydroxy compound (26) in quantitative yield. This material was directly used without further purification in the subsequent reaction. IR (KBr, diffuse reflectance) $v_{max}$ 3506, 2934, 1704, 1613 and 1518 $cm^{-1}$. NMR ($CDCl_3$) δ 0.36 (s, 3H, C-18 $CH_3$), 1.03 (t, J=7 Hz, 3H, C-21 $CH_3$), 2.84 (s, 6H, N($CH_3$)$_2$), 4.00 (s, 4H, 3-$OCH_2CH_2O$—), 4.16 (d, 1H, 11α-H) and 6.85 (dd, J=29 Hz, J'=10 Hz 4H, aromatic CH). MS (EI) m/z (relative intensity): 509 ($M^+$, 20), 491(11), 134(27) and 121(100)

Step 7. 17α-Hydroxy-21-methyl-11β-(4-N,N-dimethylaminophenyl)-19-norpregna-4,9-diene-3,20-dione (27):

The 5α,17α-dihydroxy compound (26) (3.19 g, 6.26 mmol) was dissolved in THF (25 mL). Glacial acetic acid (75 mL) was added, followed by $H_2O$ (25 mL). The mixture was stirred overnight at room temperature at which time TLC (10% acetone/$CH_2Cl_2$) showed reaction complete in the morning. The THF and acetic acid were removed under high vacuum and the residue was extracted with EtOAc (3×) and washed with saturated $NaHCO_3$ solution, $H_2O$ and brine. The combined organic extracts were dried over $Na_2SO_4$ and concentrated in vacuo to afford 2.81 g of the crude diene dione 17-alcohol (27) as a foam in 100% yield. IR (KBr, diffuse reflectance) $v_{max}$ 3419, 2942, 1705, 1655, 1612 and 1581 $cm^{-1}$. NMR ($CDCl_3$) δ 0.40 (s, 3H, C-18 $CH_3$), 1.02 (t, J=7 Hz, 3H, C-21 $CH_3$), 2.88 (s, 6H, N($CH_3$)$_3$), 4.37 (br d, 1H, 11α-H), 5.76 (s, 1H C-4H) and 6.85 (dd, J=24 Hz, J'=9 Hz, 4H, aromatic CH) MS (EI) m/z (relative intensity): 447($M^+$, 25), 211(4), 134(23) and 121 (100).

Step 8. 17α-Acetoxy-21-methyl-11β-(4-N,N-dimethylaminophenyl)-19-norpregna-4,9-diene-3,20-dione (28):

In oven-dried glassware, trifluoroacetic anhydride (18.75 mL) and glacial acetic acid (7.2 mL) were added to $CH_2Cl_2$ (50 mL) and stirred for 30 min. under nitrogen at room temperature. Solid p-toluenesulfonic acid monohydrate (1.19 g) was added and the mixture was cooled to 0° C. in an ice bath. The 17-alcohol (27) (2.77 g, 6.17 mmol) in $CH_2Cl_2$ (22 mL) was added and the reaction mixture was stirred at 0° C. for 1.5 hr. Saturated $K_2CO_3$ was carefully added dropwise until the bubbling of $CO_2$ ceased. The mixture was diluted with $H_2O$, extracted with $CH_2Cl_2$ (3×), and washed with $H_2O$ (2×) and brine. The organic layers were filtered through $Na_2SO_4$ and concentrated under reduced pressure to yield 3.12 g of the crude product (28). The crude acetate was purified by flash chromatography using 3.5% acetone/$CH_2Cl_2$ and fractions >98% pure by HPLC (70% MeOH/30% $H_2O$/0.03% TEA) were triturated in heptane to form 600 mg of a pale yellow amorphous solid in 20% yield. Analysis of the solid by HPLC using the same eluent at λ=260 nm indicated it to be 100% purity: mp=125–133° C.; $[α]^{27}_D$=+163.16° (c=1.0, $CHCl_3$). FTIR (KBr, diffuse reflectance) $v_{max}$ 1732, 1713 and 1662 $cm^{-1}$. MS (El) m/z (relative intensity): 489 ($M^+$, 27), 372(4), 251(4), 134(14) and 121 (100). NMR ($CDCl_3$) δ 0.330 (s, 3H, C-18 $CH_3$), 1.039 (t, J=7.2 Hz, 3H, C-21 $CH_3$), 2.112 (s, 3H, 17-OAc), 2.904 (s, 6H, N($CH_3$)$_2$), 4.380 (d, J=6.6 Hz, 1H, 11α-H), 5.773 (s, 1H, C-4 H), 6.635 (d, J=8.4 Hz, 2 H aromatic 3' and 5' CH) and 6.978 (d, J=8.7 Hz, 2H, aromatic 2' and 6' CH). Anal. Calcd for $C_{31}H_{39}O_4N$ C, 76.04; H, 8.03; N, 2.86; Found: C, 76.03; H, 8.05; N, 2.91.

Example VII

This example illustrates the preparation and properties of 17α-acetoxy-21-hydroxy-11β-(4-N,N-dimethylaminophenyl)-19-norpregna-4,9-diene-3,20-dione (41).

Step 1. Synthesis of 17α,21-(1-Ethoxyethylidenedioxy)-11β-(4-N,N-dimethylaminophenyl)-19-norpregna-4,9-diene-3,20-dione (18):

A solution of the 17α,21-diol (9) (1.0 g, 1.11 mmol), triethyl orthoacetate (2 mL, 10.9 mmol) and pyridinium p-toluenesulfonate (0.1 g, 0.4 mmol) in benzene (50 mL) was heated to reflux under nitrogen in a system equipped with a Dean-Stark trap for removal of water. After 1 hr of reflux, monitoring by TLC (5% acetone/$CH_2Cl_2$) indicated a complete reaction. Pyridine (1 mL, 12.4 mmol) was added and the reaction mixture concentrated in vacuo under a stream of nitrogen at 40–50° C. The residue was diluted with water (approx. 100 mL) and extracted with $CH_2Cl_2$ (3×). The combined organic extracts were washed with $H_2O$ (2×) and brine (1×), filtered through $Na_2SO_4$ and concentrated in vacuo. Purification of the residue via Flash chromatography (3% acetone/$CH_2Cl_2$) followed by crystallization from etheripentane gave 0.81 g of the intermediate ethoxyethylidenedioxy compound (18) as a white amorphous solid in 70% yield. FTIR (KBr, diffuse reflectance) $v_{max}$ 2947, 1716, 1660, 1614, 1599 and 1518 cm$^{-1}$. MS(EI) m/z (relative intensity): 519 (M$^+$, 65), 308 (23), 134(31) and 121 (100). NMR (CDCl$_3$) δ 0.33 (s, 3H, 18-CH$_3$), 1.13(t, J=7.5 Hz, 3H, OCH$_2$CH$_3$), 1.60 (s, 3H, ethylidenedioxy CH$_3$), 2.90 (s, 6H, NMe$_2$), 3.59 (q, J=7.5 Hz, 2H, OCH$_2$CH$_3$), 4.13 (dd, J$_1$=25.8, J$_2$=17.4 Hz, 2H, 21-CH$_2$), 4.43 (br. d, J=8.4 Hz, 1H, 11α-H), 5.80 (s, 1H, 4-CH), 6.67 (d, J=9 Hz, 2H, 3' and 5'-aromatic CH) and 7.07 (d, J=9 Hz, 2H, 2' and 6' aromatic CH). Anal. Calcd. for C$_{32}$H$_{41}$NO$_5$: C, 73.96: H, 7.95; N, 2.70; Found: C, 73.70; H, 7.89; N, 2.73.

Step 2. Preparation of the Target Compound (41):

Under nitrogen, a mixture of the crude ethoxyethylidenedioxy compound (18, 0.56 g., 1.11 mmol), 0.2 M NaOAc (3 mL, 0.3 mmol) in methanol (30 mL) was heated to reflux. Monitoring by TLC (5% acetone/CH$_2$Cl$_2$) indicated a complete reaction in 3.5 hours. The methanol was removed in vacuo under a stream of nitrogen, the residue diluted with water (~50 mL) and extracted with CH$_2$Cl$_2$ (3×). The organic fractions were combined, washed with H$_2$O (2×) and brine (1×), dried over Na$_2$SO$_4$, filtered and concentrated in vacuo to give 0.56 g of the crude 21-ol, 17α-acetate (41) as a foam. Purification of this material via Flash chromatography (7.5% acetone/CH$_2$Cl$_2$) followed by trituration with ether/pentane gave 0.32 g of the target compound, 21-OH, 17α-acetate as an off-white solid in 84% yield; mp=205–210° C. The NMR indicated this product contains 5.3% of the 17α-OH, 21-OAc (8) isomer as a contaminant. Compound 41 is extremely labile to base, rapidly converting to compound 8 under the reverse-phase conditions (MeOH/ H$_2$O/Et$_3$N) normally employed for HPLC analysis of related compounds. This transesterification occurs at an appreciate rate even when the solvent system is buffered at pH 7.0 with phosphoric acid. The purity of the acetate mixture (8 and 41) was ascertained at >99% by normal phase HPLC analysis (Waters Associates μPorasil Silica using CH$_3$CN/CH$_2$Cl$_2$ (40:60) with a flow rate of 2 mL/min at λ=302 nm). Under these conditions, the two acetates have an identical retention time of 4.69 min. MS (EI) m/z (relative intensity): 491 (M$^+$, 45), 431(32), 134 (7) and 121 (100). FTIR (Kr, diffuse reflectance) $v_{max}$ 3362, 2949, 2886, 1730, 1656, 1611, 1597 and 1518 cm$^{-1}$. NMR (300 MHz, CDCl$_3$) δ 0.37 (s, 3H, 18-CH$_3$), 2.11 (s, 3H, OAc), 2.90 (s, 6H, NMe$_2$), 4.23 (d, J=17.4, 1H, 21-CH$_2$), 4.36 (d, J=17.4 Hz, 1H, 21-CH$_2$), 4.39 (d, J=6 Hz, 1H, 11α-H), 5.78 (s, 1H 4-H), 6.63 (d, J32 8.7 Hz, 2H, 3' and 5' aromatic CH), 6.97 (d, J=8.7 Hz, 2' and 6' aromatic CH). The presence of the 17α-OH, 21-OAc isomer (8) to the extent of 5.3% could be detected by the appearance of two doublets, one at 4.88 and the other at 5.11, both with J=18.3 Hz.

Example VIII

This example illustrates the preparation and properties of 17α-acetoxy-21-(3'-cyclopentylpropionyloxy)-11β-(4-N,N-dimethylaminophenyl)-19-norpregnadiene-3,20-dione (40).

Step 1. 17α-Hydroxy-21-(3'-cyclopentylpropionyloxy)-11β-(4-N,N-dimethylaminophenyl)-19-norpregna-4,9-diene-3,20-dione (39):

Under nitrogen, a solution of the diol (9, 0.5 g, 1.11 mmol) in dry benzene (20 mL) and pyridine (1 mL, 12.4 mmol) was treated with 3-cyclopentylpropionyl chloride (0.2 mL, 1.31 mmol). The reaction mixture was stirred at room temperature and monitored by TLC (10% acetone/ CH$_2$Cl$_2$) which indicated about a 50% reaction after 1 hr. Additional cypionyl chloride (0.2 mL, 1.31 mmol) was introduced and the reaction was stirred a further 1 hr. at room temperature. Analysis by TLC at that time indicated a complete reaction. The reaction mixture was concentrated in vacuo under a stream of nitrogen and the residue was diluted with water. The mixture was extracted with CH$_2$Cl$_2$ (3×). The organic fractions were combined, and washed with H$_2$O (2×), brine (1×), dried (Na$_2$SO$_4$), filtered and concentrated in vacuo to give 0.63 g of the residue as an oil. Purification of this material by Flash chromatography using 7% acetone/ CH$_2$Cl$_2$ gave 0.51 g of the 17α-hydroxy 21-cypionate (39) as an oil. Trituration of this material with ether afforded 0.43 g of a pure solid (39) in 67% yield; mp=137–140° C. MS (EI) m/z relative intensity: 573 (M$^+$, 46), 431 (11), 134 (15) and 121 (100). FTIR (KBr, diffuse reflectance) $v_{max}$ 3509, 2944, 1726, 1643, 1613 and 1520 cm$^{-1}$. NMR (CDCl$_3$) δ 0.38 (s, 3H, 18-CH$_3$), 2.90 (s, 6H, NMe$_2$), 4.4 (br d, J=6 Hz, 11α-H), 5.03 (dd, J$_1$=31.5 Hz, J$_2$=18 Hz, 2H, 21-CH2-OCyp), 5.76 (s, 1H 4-CH), 6.67 (d, J=9 Hz, 2H, aromatic 3' and 5' CH) and 7.07 (d, J=9 Hz, 2H, aromatic 2' and 6' CH).

Step 2. 17α-Acetoxy-21-(3'-cyclopentylpropionyloxy)-11β-(4-N,N-dimethylaminophenyl)-19-norpregna-4,9-diene-3,20-dione (40):

Under nitrogen, trifluoroacetic anhydride (2.0 mL, 14.2 mmol), glacial acetic acid (0.8 mL, 13.99 mmol) and dry CH$_2$Cl$_2$ (10 mL) were combined and stirred at room temperature for ½ hr. The mixture was cooled to 0° C. in an ice bath and p-toluenesulfonic acid monohydrate (1 g, 0.53 mmol) was added to it. A solution of the 17α-hydroxy-21-cypionate (39, 0.4 g, 0.7 mmol) in dry CH$_2$Cl$_2$ was then introduced and the reaction mixture stirred at 0° C. and monitored by TLC (5% acetone/CH$_2$Cl$_2$). After 2 hr. at 0° C. it became apparent that this particular reaction was proceeding at a much slower rate than observed for other 17α-acetylations. The ice-bath was removed and the reaction was then stirred and monitored by TLC at room temperature. After 6 hr. at room temperature, TLC indicated ~75% conversion. The reaction mixture was then diluted with H$_2$O (10 mL), neutralized with concentrated NH$_4$OH solution and extracted with CH$_2$Cl$_2$ (3×). The organic fractions were combined, washed with H$_2$O (2×), brine (1×), filtered through Na$_2$SO$_4$ and concentrated in vacuo to give 0.53 g of the residue as an oil. Purification via Flash chromatography (5% acetone/CH$_2$Cl$_2$) gave 0.21 g of the pure 17-acetate (40) as a foam. This material was dissolved in EtOH (~2 mL) and precipitated as a yellow amorphous solid upon dilution with H$_2$O, sonication and cooling to give 0.21 g of the pure solid (40) in 28% yield: mp. softens at 96° C. MS (EI) m/z (relative intensity): 615 (M$^+$, 80), 555 (10), 372 (18), 134 (14) and 120 (100) FTIR (KBr, diffuse reflectance) $v_{max}$ 2950, 2868, 1737, 1664, 1612 and 1519 cm$^{-1}$. NMR (CDCl3) δ 0.43 (s, 3H 18-CH$_3$), 2.11 (s, 3H, OAc), 2.91 (s, 6H, NMe$_2$), (br d, J=6 Hz, 11α-H), 4.84 (dd, J=29 Hz, J$_2$=17 Hz, 2H, 21-CH$_2$—OCyp), 5.80 (s, 1H, 4-CH), 5.80 (s, 1H, 4-CH), 6.70 (d, J=9 Hz, 2H, aromatic 3' and 5' CH) and 7.07 (d, 9 Hz, 2H, aromatic 2' and 6' CH). Anal. Calcd. for C$_{38}$H$_{49}$NO$_6$.¼ C$_5$H$_{12}$; C, 74.38; H, 8.27; N, 2.21; Found: C, 74.39; H, 8.28; N, 2.20.

Example IX

This example illustrates the preparation and properties of 17α-acetoxy-21-methoxy-11β-(4-N,N-dimethylaminophenyl)-19-norpregna-4,9-diene-3,20-dione (38).

Step 1. 17α-Bromomethyldimethylsilyloxy-17β-cyano-3, 3-ethylenedioxyestra-5(10),9(11)-diene (29):

Under nitrogen and anhydrous conditions, a solution of the cyanohydrin ketal (1, 35.45 g (104 mmol)), dimethylaminopyridine (6.33 g, 52 mmol) and dry Et$_3$N (21.7 mL, 155 mmol) in dry THF (300 mL) was stirred at room temperature overnight. After that time, TLC using 2% acetone/CH$_2$Cl$_2$ indicated approximately 95% completion of reaction. The mixture was diluted with hexanes (~250 mL), stirred at ~10 minutes, filtered through Celite and concentrated in vacuo to give the residue (46.38 g) evidenced by TLC to consist of a mixture of the expected product (29) plus DMAP hydrochloride salt. This material was purified via silica Flash chromatography using ether as eluent to give the silyl ether (29, 35.53 g, 69.5% ). This material was used directly in the subsequent reaction without further purification or characterization.

Step 2. 17α-Hydroxy-21-bromo-19-norpregna-4,9-diene-3,20-dione (30):

Under nitrogen, a solution of the crude 17α-bromo compound (29, 35.53 g, 72 mmol) in dry THF (1200 mL) was cooled to −78° C. in a dry ice/isopropanol bath and treated dropwise with a 1.5 M solution of lithium diisopropylamide in cyclohexane (105 mL, 157.5 mmol) over a period of ~15 minutes. This mixture was stirred at −78° C. for 1 hr. Aqueous HBr (4.45 M, 350 mL, 1.56 mol) was added slowly and the mixture allowed to warm to room temperature, and stirred for 30 min. A TLC using 5% acetone/CH$_2$Cl$_2$ taken at that time indicated an incomplete reaction (3 products). The mixture was then stirred again at room temperature overnight. Analysis by TLC at that time indicated formation of 1 major product. The reaction mixture was then cooled in an ice bath, carefully neutralized with concentrated NH$_4$OH solution (105 mL) and extracted with EtOAc (3×). The organic fractions were washed with H$_2$O (2×), combined, dried over Na$_2$SO$_4$ and concentrated in vacuo. Trituration of the solid residue with ether gave the 17α-hydroxy-21-bromo compound (30, 17.14 g) in 60.4% yield as an off-white powder. FTIR (Kfr, diffuse reflectance) ν$_{max}$ 3476, 2948, 1726, 1644, 1598 and 1572 cm$^{-1}$. NMR (DMSO-d$_6$+CDCl$_3$) δ 0.70 (s, 3H, 18-CH$_3$), 4.43 (dd J$_1$=27 Hz, J$_2$=15 Hz, 2H, 21-CH$_2$Br) and 5.60 (s, 1H, 4-H). MS (EI) m/z (relative intensity): 392(M$^+$, 11), 313 (100), 159 (77) and 91 (71).

Step 3. 17α-hydroxy-21-acetoxy-19-norpregna-4,9-diene-3,20-dione (31:

The 21-bromo-17α-hydroxy compound (30, 6.57 g, 16.7 mmol) was added to a 3-neck 1 L flask which had been purged with nitrogen, equipped with a condenser and a magnetic stir bar. Acetone (500 mL) was added, followed by potassium acetate (17.3 g, 176.2 mmol). The suspension was stirred magnetically and brought to reflux under nitrogen. Several minutes after reaching reflux, a solution formed. After ½ hr, the reaction was examined by TLC (silica: 5% acetone in CH$_2$Cl$_2$). All starting material had been converted to the product. The reaction was allowed to cool to room temperature, precipitated KBr was removed by filtration, and the solution evaporated in vacuo. The crude product (6.63 g) was obtained, taken up in CH$_2$Cl$_2$ and washed with H$_2$O (2×), followed by brine (1×). The combined organic extracts were filtered through Na$_2$SO$_4$ and evaporated in vacuo to obtain 6.41 g of the 21-acetoxy-17α-hydroxy compound (31in 99% yield. FTIR (KBr, diffuse reflectance) ν$_{max}$ 3474, 2946, 1744, 1720, 1645 and 1607 cm$^{-1}$. NMR (CDCl$_3$) δ 0.80 (s, 3H, 18-CH$_3$), 2.13 (s, 3H C-12-OAc), 5.0 (dd, 2H, C-21-CH$_2$, J$_1$=24 Hz, J$_2$=9Hz) and 5.68 (s, 1H, 4-H) MS (EI) m/z (relative intensity): 372 (M$^+$, 55), 312 (68), 271(69), 253 (97) and 213 (100).

Step 4. 17α,21-Dihydroxy-19-norpregna-4,9-diene-3,20-dione (32):

A suspension of the 21-acetoxy-17α-hydroxy compound (31, 9.43 g, 25.32 mmol) in MeOH (800 mL) was deoxygenated by purging with nitrogen for ½ hr. A similarly deoxygenated 0.5 M solution of KHCO$_3$ (78 mL, 39 mmol) was added to the suspension and the mixture brought to reflux under nitrogen. Almost immediately after addition of KHCO$_3$, a solution formed. After ½ hr at reflux, the reaction mixture was examined by TLC (silica; 5% isopropanol in CH$_2$Cl$_2$). The reaction was >95% complete. The reaction was allowed to cool to room temperature, then neutralized by addition of 2.24 mL (39 mmol) of glacial acetic acid. CH$_3$OH was evaporated in vacuo. The residue was taken up in 500 mL of CH$_2$Cl$_2$ and washed with H$_2$O (3×). Combined organic extracts were dried by filtration through Na$_2$SO$_4$, and evaporated in vacuo to recover an amorphous yellow material (8.50 g, 32) in 100% yield. This material was readily crystallized from hot acetone (100 mL). The crystals were collected on a Buchner funnel, triturated well with ether, and air dried. It gave 4.82 g of 32 in 57.6% yield. Additional material was obtained by chromatography of the mother liquors, FTIR (KBr, diffuse reflectance) ν$_{max}$ 3517, 2944, 1714, 1657, 1598 and 1578 cm$^{-1}$. NMR (CDCl$_3$) δ 0.82 (s, 3H, 18-Me), 4.53 (dd, 2H, C-21-CH$_2$—, J$_1$=42 Hz, J$_2$=21 Hz), 5.72 (s, 1H, 4-H). MS (EI) m/z (relative intensity): 330 (M$^+$, 100), 253 (83), 228 (98), 213 (95) and 91 (91).

Step 5. 3,20-bis-Ethylenedioxy-17α,21-dihydroxy-19-norpregna-5(10),9(11)-diene (33):

A quantity of 3.8 g (11.5 mmol) of the 17α,21-dihydroxy compound, 200 mg (1.05 mmol) of p-toluenesulfonic acid, and 300 mL of ethylene glycol were placed in a 500 mL of round bottom flask equipped with a vacuum distillation head. The mixture was heated in an oil bath and the temperature was maintained at 100–105° C. Ethylene glycol was distilled in vacuo (5 mm Hg), at a temperature of 75° C. The reaction continued for 3 hr. and was allowed to cool to room temperature. Saturated NaHCO$_3$ solution was added and the mixture extracted with CH$_2$Cl$_2$. The organic extract was washed with H$_2$O (1×) and brine (1×). The organic extracts were dried by filtration through Na$_2$SO$_4$ and evaporated in vacuo. Crude diketal (6.2 g) was obtained. Examination of this material by TLC (silica, 5% isopropanol in CH$_2$Cl$_2$) indicated almost all starting material had been converted to the diketal as a major product with R$_f$=0.38, an intermediate product as a minor product with R$_f$=0.63, or a third material with R$_f$=0.63 which increases if the reaction is allowed to go too long. The crude material was crystallized from 30 mL of hot CH$_2$Cl$_2$. The crystals were collected on a Buchner funnel, triturated well with ether and air dried to give 3.01 g of 33 in 62.5% yield. This product was considered sufficiently pure to be carried out on the next reaction. Highly pure material was obtained by flash column chromatography using 5% isopropanol in CH$_2$Cl$_2$. FTIR (KBr, diffuse reflectance): 3418 and 2896 cm$^{-1}$; no evidence of any absorptions in the CO region. NMR (CDCl$_3$) δ 0.8 (s, 3H, 18-CH$_3$), 3.88 (m, 10H, C-3 and C-20-OCH$_2$CH$_2$O—, C-21-CH$_2$), 4.0 (s, 4H, C-3-OCH$_2$CH$_2$)—), 5.58 (br s, 1H, 11-H). MS (EI) m/z (relative intensity): 418 (M$^+$, 2), 387 (1.4), 297 (3) and 103 (100).

Step 6. 3,20-bis-(Ethylenedioxy)-17α-hydroxy-21-methoxy-19-norpregna-5(10),9(11)-diene (34):

To a solution of the 17α,21-dihydroxy diketal (33, 2,0 g, 4.78 mmol) in CH$_2$Cl$_2$ (250 mL) was added 7.20 g (33.6 mmol) of solid 1,8-bis(dimethylamino)-naphthalene ("proton sponge") followed by 4.97 g (33.6 mmol) of trimethyloxonium tetrafluoroborate. The heterogeneous mixture was stirred in an ice bath under nitrogen, and allowed to come to room temperature as the bath melted. After 2.5 hr., TLC (silica; 5% isopropanol in CH$_2$Cl$_2$)

indicated the reaction was complete. The mixture was transferred to a separatory funnel and washed with ice cold 1N HCl (250 mL), saturated NaHCO$_3$ solution and H$_2$O. The combined organic extracts (3×) were dried by filtration through solid Na$_2$SO$_4$ and evaporated in vacuo. Examination by TLC indicated the resulting yellow oil was heavily contaminated with a base. The oil was taken up in CH$_2$Cl$_2$ (75 mL) and stirred vigorously with Dowex 50×8–200 (80 mL, dry volume) for 15 minutes. This effectively removed all the remaining proton sponge. The mixture was filtered and the Dowex washed well with CH$_2$Cl$_2$. Methylene chloride was evaporated in vacuo and the residue dried overnight under high vacuum to give a pale foam, 1.63 g in 79% yield. This material was sufficiently pure to carry on to the next reaction. Highly pure material was obtained by flash column chromatography eluting with 20% EtOAc in CH$_2$Cl$_2$, followed by crystallization from a small amount of methanol with water. FTIR (KBr, diffuse reflectance) $v_{max}$ 3510, 2898, 1720, 1450 and 1370 cm$^{-1}$. NMR (CDCl$_3$) δ 0.8 (s, 3H, 18-CH$_3$), 3.43 (s, 3H,C21-OCH$_3$), 3.67 (dd, 2H, C21-CH2, J32 18 Hz, J$_2$=10.5 Hz), 4.0 (s, 4H, C- 3-OCH$_2$CH$_2$O), 4.09 (m, 8H, C-3 and C-20-OCH$_2$CH$_2$O) and 5.58 (br s, 1H, C-11 H). MS (EI) m/z (relative intensity): 432 (M$^+$, 1.4), 387 (3), 297 (2.6) and 117 (100).

Step 7. 3,20-bis-(Ethylenedioxy)-5α,10α-epoxy-17α-hydroxy-21-methoxy-19-norpregn-9(11)-ene (35):

Solid Na$_2$HPO$_4$ (0.45 g, 3.14 mmol) and 30% H$_2$O$_2$ (0.84 mL) were added to a vigorously stirred solution of hexafluoroacetone trihydrate (1.24 g, 0.79 mL, 5.7 mmol) in CH$_2$Cl$_2$ (13 mL). The mixture was stirred under nitrogen in an ice bath for ½ hr. A chilled solution of the 21-methoxy-17α-hydroxy compound (34, 1.63 g, 3.77 mmol) in CH$_2$Cl$_2$ (13 mL) was added slowly via pipette. The reaction was transferred to the cold room and allowed to stir overnight at 4° C. The next morning, examination by TLC (silica; 25% EtOAc in CH$_2$Cl$_2$) indicated all starting material had been converted to a mixture of two more polar components. Methylene chloride (25 mL) was added and the mixture washed with 10% Na$_2$SO$_3$ (2×), saturated NaHCO$_3$ solution and H$_2$O. The combined organic extracts (3×) were dried by filtration through Na$_2$SO$_4$, evaporated in vacuo and dried several hours under high vacuum to give 1.86 g of an amorphous solid in quantitative yield, which consists of at least, 4 epoxides evidenced by $^1$H NMR. NMR (CDCl$_3$) δ 0.77 (s, 3H , 18-CH$_3$), 3.40 (s, 3H, C-21 OCH$_3$), 3.60 (dd, C-21-CH$_2$, J$_1$=15 Hz, J$_2$=9 Hz), 3.9 (s, C-3-OCH$_2$CH$_2$O), 4.0 (m, C-3- and -OCH$_2$CH$_2$O), 5.83 (br s, 11β-H) and 6.03 (br s, 11α-H).

Step 8. 3,20-bis-(Ethylenedioxy)-5α,17α-dihydroxy-11β-(4-N,N-dimethylaminophenyl)-21-methoxy-19-norpregn-9 (10)-ene (36):

A 100 mL round bottom flask was equipped with a magnetic stirrer, a reflux condenser and a rubber septum and flame dried under a stream of N$_2$. Magnesium (0.50 g, 20.7 mmol) was added, followed by a crystal of iodine, dry THF (20 mL) and 1–2 drops of dibromoethane. The mixture was heated in a warm H$_2$O bath under N$_2$ for approximately ½ hr, but there were no observable change. A solution of 4-bromo-N,N-dimethylaniline (3.77 g, 18.85 mmol) in THF (10 mL) was added via syringe over a period of several minutes and rinsed with an additional THF (10 mL). There was evidence of reaction immediately as the magnesium turned dark. After stirring for 1.5 hr., solid copper(I) chloride (0.21 g, 2.07 mmol), was added and the reaction mixture stirred another ½ hr. Crude epoxide (assumed 3.77 mmol from the previous reaction) was added as a solution in THF (5 mL) and rinsed in with an additional THF (5 mL). The reaction was allowed to stir one hr at room temperature and then quenched by the addition of saturated ammonium chloride (50 mL). Air was drawn through the mixture with vigorous stirring for ½ hr. Ether was added and the layers allowed to separate. The organic solution was washed with 10% NH$_4$Cl (2×), 2 N NH$_4$OH (3×) and brine (1×). Organic fractions were combined, dried over Na$_2$SO$_4$, filtered and evaporated in vacuo to obtain 3.37 g of crude material. Analysis by TLC (silica; 20% acetone in CH$_2$Cl$_2$) indicated formation of a new more polar compound. Flash column chromatography (silica; 20% acetone in CH$_2$Cl$_2$), yielded 0.890 g of the pure product in 63% yield, assuming 66% of the starting material was the desired 5α, 10-α-epoxide). FTIR (KBr, diffuse reflectance) $v_{max}$ 3494, 2936, 1612 and 1518 cm$^{-1}$. NMR (CDCl$_3$) δ 0.47 (s, 3H, 18-CH$_3$), 2.90 (s, 6H, —N(CH$_3$)$_2$), 3.43 (s, 3H, C-21-OCH$_3$), 4.03 (m, 10H, C-3 and C-20-OCH$_2$CH$_2$O— and C-21-CH$_2$), 6.67 (d, 2H, aromatic, J=9 Hz), and 7.10 (d, 2H, aromatic, J=9 Hz). MS (EI) m/z (relative intensity): 569 (M$^+$, 4), 551 (11), 506 (4), 134 (27), 121 (49) and 117 (100).

Anal. Calcd. for C$_{33}$H$_{47}$O$_7$N: C, 69.57; H, 8.31; N, 2.46; Found: C, 69.40; H, 8.19; N. 2.53.

Step 9. 17α-Hydroxy-21-methoxy-11β-(4-N,N-dimethylaminophenyl)-19-norpregna-4,9-diene-3,20-dione (37):

The diketal (36, 1.81 g, 3.18 mmol) was dissolved in THF (20 mL) and the solution stirred magnetically at room temperature under nitrogen. Trifluoroacetic acid (60 mL) was added followed by H$_2$O (20 mL). After 1 hr., the reaction was examined by TLC (silica; 20% acetone in CH$_2$Cl$_2$; neutralized with conc. NH$_4$OH before developing). All starting material had been converted to the product. The reaction was neutralized by the careful addition of conc. NH$_4$OH (55 mL). Enough additional NH$_4$OH was added to bring the pH between 6 and 7. The product was extracted by CH$_2$Cl$_2$ (3×). The organic extracts were combined, washed with H$_2$O (1×) and dried by filtration through Na$_2$SO$_4$. Evaporation in vacuo followed by drying overnight under high vacuum gave 37 as an amber glass (1.42 g, 96.3% ). The resulting oil was crystallized by trituration with H$_2$O and scratching and sonicating to produce a fine bright yellow powder. FTIR (KBr, diffuse reflectance) $v_{max}$ 3408, 2943, 1722, 1663, 1612 and 1518 cm$^{-1}$. NMR (CDCl$_3$) δ 0.37 (s, 3H, 18-CH$_3$), 2.90 (s, 6H, —N(CH$_3$)$_2$), 3.43 (s, 3H, C-21-OCH$_3$), 4.43 (dd, 2H, C-21-CH$_2$,J$_1$=27 Hz, J$_2$=18 Hz), 5.77 (s, 1H, C-4), 6,65 (d, 2H, aromatic J=9 Hz) and 7.03 (d, 2H, aromatic, J=9 Hz). MS (EI) m/z (relative intensity): 463 (M$^+$, 20), 134 (21) and 121 (100). Anal. Calcd. for C$_{29}$H$_{37}$O$_4$N.⅔ H$_2$O: C, 73.23; H, 8.12; N, 2.94; Found: C, 73.09; H, 7.88; N, 2.97.

Step 10. Preparation of the Target Compound (38):

A mixture of CH$_2$Cl$_2$ (35 mL), trifluoroacetic anhydride (6.0 mL) and glacial acetic acid (2.43 mL) was allowed to stir at room temperature under nitrogen. After ½ hr, the mixture was cooled to 0° C. in an ice water bath and p-toluenesulfonic acid (350 mg) was added. A solution of the 17α-hydroxy-21-methoxy compound (37, 730 mg, 1.57 mmol) was added in CH$_2$Cl$_2$ (4 mL) and rinsed in with CH$_2$Cl$_2$ (2×4 mL). After stirring 1.5 hr at 0° C., examination by TLC (silica; 10% acetone in CH$_2$Cl$_2$, after neutralization by NH$_4$OH) indicated the reaction was >95% complete. The reaction mixture was diluted with H$_2$O (35 mL) and neutralized with concentrated NH$_4$OH. The product was extracted by CH$_2$Cl$_2$ (3×) and brine (1×). The combined organic extracts were dried by filtration through Na$_2$SO$_4$ and evaporated in vacuo to give 0.91 g of the crude product.

Flash column chromatography on silica using 10% acetone in $CH_2Cl_2$ followed by evaporation in vacuo and drying under high vacuum produced 38 as a pure pale yellow foam (0.6 g, 75.8%). Treatment with pentane followed by sonicating produced a fine powder: m.p. softens at 116° C. HPLC analysis on a NovaPak $C_{18}$ column eluting with 70% $CH_3OH$ in $H_2O$ with 0.03% $Et_3N$ at a flow rate of 1 mL per min at λ=302 indicated the product 38 to be 98.06% pure with a retention time of $R_f$=5.08 min. FTIR (diffuse reflectance, KBr): $v_{max}$ 2940, 1734, 1663, 1612, 1518, 1446, 1370, 1235, and 1124 $cm^{-1}$. NMR ($CDCl_3$) δ 0.38 (s, 3H, 18-$CH_3$), 2.08 (s, 3H, OAc), 2.90 (s, 6H, $NMe_2$), 3.42 (s, 3H, 21-$OCH_3$), 4.20 (dd, 2H, C-21-$CH_2$, $J_1$=24 Hz, $J_2$=15 Hz), 5.80 (s, 1H, C-4-H), 6.67 (d, 2H, aromatic, J=9 Hz) and 7.0 (d, 2H, aromatic, J=9 Hz). MS (EI) m/z (relative intensity): 505 ($M^+$, 75), 445 (1.1), 430 (8%), 372(2.7), 134 (16) and 121 (100) Anal. Calcd. for $C_{31}H_{39}O_5N$; C, 73.64; H, 7.77; N, 2.77; Found: C, 73.34; H, 7.74; N, 2.70.

Example X

This example illustrates the preparation and properties of 17α-acetoxy-21-ethoxy-11β-(4-N,N-dimethylaminophenyl)-19-norpregna-4,9-diene-3,20-dione (46).

Step 1. 3,20-bis-(Ethylenedioxy)-17α-hydroxy-21-ethoxy-19-norpregna-5(10),9(11)-diene (42):

To a cold solution of the 17α,21-dihydroxy diketal (33, 5.66 g, 13.53 mmol) in $CH_2Cl_2$ (700 mL) in an ice bath under nitrogen was added 20.3 g (94.7 mmol) of solid 1,8-bis-(dimethylamino)naphthalene ("proton sponge"), followed by triethyloxonium tetrafluoroborate (18.0 g, 94.7 mmol). The reaction mixture was allowed to gradually warm to room temperature as the ice bath melted. After 1 hr, TLC (silica; 5% isopropanol in $CH_2Cl_2$) indicated the reaction was >95% complete. The reaction was quenched after a total time of 2 hr by the addition of $H_2O$. The mixture was transferred to a separatory funnel and washed with $H_2O$ (2×). The combined organic fractions were dried by filtration through $Na_2SO_4$ and evaporated in vacuo. The resulting residue was taken up in EtOAc and washed with ice cold 1 N HCl (2×), saturated $NaHCO_3$ and $H_2O$. Combined organic fractions were filtered through $Na_2SO_4$ and evaporated in vacuo to recover 6.86 g of an oil. Purification of this oil by flash column chromatography on silica using 5% acetone in $CH_2Cl_2$ gave 4.37 g of a colorless foam in 72.4% yield: mp=softens at 62° C. FTIR (KBr, diffuse reflectance) $v_{max}$ 3485, 2889, 2738, 1440, 1371, 1216, 1120 and 1058 $cm^{-1}$. NMR(300 MHZ, $CDCl_3$) δ 0.8 (s, 3H, 18-$CH_3$), 1.22 (t, 3H, C-21O$CH_2CH_3$, J=6.9 Hz), 3.0 (s, 1H, C-17 OH), 3.46–3.82 (m, 4H, C-21 CH2 and C-21 O$CH_2$$CH_3$), 3.98 (s, 4H, C-3 O$CH_2CH_2$O), 3.84–4.28 (m, 8H, C-3 and C-20 O$CH_2CH_2$O), and 5.55 (br s, 1H, C-11H). MS (EI) m/z (relative intensity): 446($M^+$, 2), 400 (0.9), 387 (6.6), 369 (2.8), 297 (5.5) and 131 (100).

Step 2. 3,20-bis-(Ethylenedioxy)-5α,10α-epoxy-17α-hydroxy-21-ethoxy-19-norpregn-9(11)-ene (43):

To a solution of hexafluoroacetone trihydrate (2.05 mL, 14.7 mmol) in $CH_2Cl_2$ (35 mL), was added solid $Na_2HPO_4$ (1.17 g, 8.24 mmol) followed by 30% $H_2O_2$ (2.2 mL). The mixture was stirred vigorously in an ice bath under nitrogen for ½ hr. A chilled solution of the 21-ethoxy-17α-hydroxy compound (42, 4.37 g, 9.79 mmol) in $CH_2Cl_2$ (35 mL) was added slowly via pipette. The reaction was transferred to the cold room and allowed to stir overnight at 4° C. The next morning, examination of the reaction mixture by TLC (silica; 5% acetone in $CH_2Cl_2$) indicated all of the starting material had been converted to two more polar components in approximately a 2:1 ratio. The reaction mixture was transferred to a separatory funnel and washed with 10% $Na_2SO_3$ (2×), saturated $NaHCO_3$, $H_2O$ and brine. The combined organic fractions were filtered through $Na_2SO_4$ and evaporated in vacuo to recover 4.84 g of a colorless foam. Trituration of this crude product with $Et_2O$ produced a white solid. The solid was collected on a Buchner funnel and dried overnight in vacuo to give 1.73 g of white crystals in 38.1% yield. Examination of this material by TLC and NMR indicated it was pure 5α,10α-epoxide (43). Purification of the mother liquors by flash column chromatography on silica eluting with 7% acetone in $CH_2Cl_2$ gave an additional 0.6 g of 5α,10α-epoxide (43). Total yield of purified 5α,10α-epoxide (43) was 2.33 g (51.3%): mp=154–166° C. dec. FTIR (KBr, diffuse reflectance) $v_{max}$ 3566, 2934, 2890, 2441, 1375, 1212, 1118, 1064 and 1044 $cm^{-1}$. NMR ($CDCl_3$) δ 0.78 (s, 3H, C-18 $CH_3$), 1.2 (t, 3H, C-21 O$CH_2CH_3$, J=6 Hz), 2.88 (s, 1H, C-17 OH), 3.33–3.73 (m, 4H, C-21 $CH_2$ and C-21 O$CH_2$$CH_3$), 3.93 (s, 4H, C-3 O$CH_2CH_2$O), 3.73–4.27 (m, 8H, C-3 and C-20 O$CH_2CH_2$O), 6.03 (br, s, 1H, C-11 CH). MS (EI) m/z (relative intensity): 462 ($M^+$, 1.1), 403 (8.9), 385 (5.9), 131 (100) and 87 (32).

Step 3. 3,20-bis-(Ethylenedioxy)-5α,17α-dihydroxy-11β-(4-N,N-dimethylaminophenyl)-21-ethoxy-19-norpregn-9(10)-ene (44):

A three-neck round bottom flask (250 mL) was equipped with a magnetic stirrer, a condenser, a glass stopper and a rubber septum and flame dried under a stream of nitrogen. Magnesium was added (655 mg, 24.5 mmol), followed by a crystal of iodine, 25 mL of dry THF, and 1–2 drops of dibromoethane. After heating in a warm water bath for approximately ½ hr under nitrogen, no observable change occurred. A solution of 4-bromo-N,N-dimethylaniline (4.9 g, 24.5 mmol) in 13 mL of dry THF was added via syringe over a period of several minutes and rinsed in with an additional 13 mL of THF. A reaction occurred almost immediately as the THF began to reflux and the surface of the magnesium turned dark. Approximately 10 min. after the addition of the 4-bromo-N,N-dimethylaniline, heating was discontinued, but the reaction was allowed to remain in the bath. After stirring for 1.5 hr, copper (I) chloride (267 mg, 2.7 mmol) was added as a solid and stirring continued for another ½ hr. The 5α,10α-epoxide (43, 2.27 g, 4.9 mmol) was added via syringe as a solution in 6.5 mL of dry THF and rinsed in with 6.5 mL of THF. After 2 hr, examination of the reaction mixture by TLC on silica (20% acetone in $CH_2Cl_2$; quenched with saturated $NH_4Cl$ before developing) indicated all epoxide had been converted to a new more polar material. The reaction was quenched by the addition of saturated $NH_4Cl$ (65 mL) and air was drawn through the mixture for ½ hr with vigorous stirring. The reaction mixture was transferred to a separatory funnel, ether added, and the layers allowed to separate. The organic fraction was washed with 10% $NH_4Cl$ (1×), 2 N $NH_4OH$ (1×) and brine (1×). The combined organic fractions (3×) were filtered through $Na_2SO_4$ and evaporated in vacuo to obtain 5.62 g of crude material. This crude product was purified by flash column chromatography on silica. The column was first washed with $CH_2Cl_2$ to remove impurities with high $R_f$ before eluting the product with 20% acetone in $CH_2Cl_2$. Appropriate fractions were combined and evaporated in vacuo to give a crystallizing oil. Crystallization of this material from a minimum amount of hot ether afforded 2.09 g of a pale blue powder (44) in 73% yield; mp=199–201° C. dec. FTIR (KBr, diffuse reflectance) $v_{max}$ 3591, 3529, 3421, 2971, 2882, 1615, 1562, 1519, 1443, 1354, 1190, 1122 and 1053 cm$^{-1}$. NMR (CDCl$_3$) δ 0.47 (s, 3H, C-18 CH$_3$), 1.23 (t, 3H, C-21 OCH$_2$CH$_3$, J=6 Hz), 2.90 (s, 6H, —N(CH$_3$)$_2$), 3.43–3.80 (m, 4H, C-21 CH2 and C-21 OCH$_2$CH$_3$), 3.80–4.33 (m, 9H, C-3 and C-20-OCH$_2$CH$_2$O—, and C-11 CH), 6.67 (d, 2H, aromatic, J=9 Hz), 7.10 (d, 2H, aromatic, J=9 Hz). MS (EI) m/z (relative intensity): 538 (M$^+$, 14), 565(19), 506 (13) and 131(100). Anal. Calcd. for C$_{34}$H$_{49}$O$_7$N:C, 69.96; H, 8.46; N, 2.40. Found: C, 69.78; H, 8.37; N, 2.35.

Step 4. 17α-Hydroxy-21-ethoxy-11β-(4-N,N-dimethylaminophenyl)-19-norpregna-4,9-diene-3,20-dione (45):

The dihydroxy diketal (44, 2.0 g, 3.43 mmol) was dissolved in THF (20 mL) and stirred magnetically at room temperature under nitrogen. Trifluoroacetic acid (60 mL) was added followed by H$_2$O (20 mL). After 40 min, TLC (20% acetone in CH$_2$Cl$_2$, neutralized with conc. NH$_4$OH before developing) indicated the reaction had gone to completion. The reaction was allowed to continue another hour before neutralizing by the careful addition of conc. NH$_4$OH (55 mL). Additional NH$_4$OH was added to bring the pH to 6–7, CH$_2$Cl$_2$ was added, the mixture transferred to a separatory funnel, and the layers allowed to separate. The organic phase was washed again with H$_2$O (1×), and brine (1×). Combined CH$_2$Cl$_2$ extracts (3×) were filtered through Na$_2$SO$_4$ and evaporated in vacuo to give 1.73 g of an amber foam. Purification by flash column chromatography on silica eluting with 20% acetone in CH$_2$Cl$_2$ afforded 1.28 g of pure 45 as a bright yellow foam in 78% yield: mp=softens at 96° C. FTIR (KBr, diffuse reflectance) ν$_{max}$ 3440, 2944, 2880, 1721, 1658, 1612, 1518, 1443, 1347, 1211 and 1136 cm$^{-1}$. NMR (CDCl$_3$) δ 0.40 (s, 3H, C-18 CH$_3$), 1.3 (t, 3H, C-21 OCH$_2$CH$_3$, J=6 Hz), 2.93 (s, 6H, —N(CH$_3$)$_2$), 3.4–3.8 (m, 3H, C-21 OCH$_2$CH$_3$ and C-17 OH), 4.13–4.63 (m, 3H, C-21 CH$_2$ and C-11 CH), 5.80 (s, 1H, C-4 CH), 6.68 (d, 2H, aromatic, J=9 Hz), 7.05 (d, 2H, aromatic, J=9 Hz). MS (EI) m/z (relative intensity): 477 (M$^+$, 42), 280 (14), 134 (26) and 121 (100). Anal. Calcd. for C$_{30}$H$_{39}$O$_4$N.⅓H$_2$O: C, 74.50; H, 8.21; N, 2.90. Found: C, 74.46; H, 8.2; N, 2.93.

Step 5. Preparation of the Target Compound (46):

A mixture of trifluoroacetic anhydride (9.77 mL), and glacial acetic acid (3.9 mL) in CH$_2$Cl$_2$ (50 mL) was allowed to stir ½ hr under nitrogen at room temperature. The mixture was cooled to 0° C. in an ice bath and toluenesulfonic acid monohydrate (0.57 g, 3 mmol) was added. A solution of the 17α-hydroxy-21-ethoxy compound (45, 1.22 g, 2.55 mmol) in CH$_2$Cl$_2$ (10 mL) was added to the above mixture, and then rinsed in with 10 mL of CH$_2$Cl$_2$. After stirring 2 hr at 0° C., the reaction was examined by TLC (silica; 10% acetone in CH$_2$Cl$_2$, neutralized with conc. NH$_4$OH before developing) and was found to be >95% complete. The reaction mixture was diluted with H$_2$O (50 mL) and neutralized by the careful addition of conc. NH$_4$OH. More CH$_2$Cl$_2$ and H$_2$O were added, the mixture was transferred to a separatory funnel, and the layers allowed to separate. The organic fraction was washed again with H$_2$O and brine. Combined CH$_2$Cl$_2$ extracts (3×) were filtered through Na$_2$SO$_4$ and evaporated in vacuo to give 1.35 g of an amber foam. This crude product was purified twice by flash column chromatography on silica eluting with 8% acetone in CH$_2$Cl$_2$. Appropriate fractions were combined, evaporated in vacuo, chased with ether to obtain 0.81 g of a foam. Treatment with pentane produced a pale yellow powder. The powder was dried overnight in vacuo at 58° C. to remove all traces of solvent. Total yield of pure 46 was 491 mg in 37% ; mp=softens at 104° C. HPLC analysis on Phenomenex Prodigy 5 ODS-2 column (150×4.6 mm) eluting with 30% H$_2$O with 0.03% triethylammonium phosphate (pH 7.0) in CH$_3$OH at a flow rate of 1 mL per min at λ=302 indicated the product 46 to be 98.76% pure with a retention time (R$_T$) of 16.64 min. FTIR (KBR, diffuse reflectance) ν$_{max}$ 2945, 2890, 1734, 1663, 1612, 1562, 1518, 1446, 1368 and 1235 cm$^{-1}$. NMR (CDCl$_3$) δ 0.43 (s, 3H, C-18 CH$_3$), 1.28 (t, 3H, C-21 —OCH$_2$CH$_3$, J=6 Hz), 2.15 (s, 3H, C-17 OAc), 2.95 (s, 6H, —N(CH$_3$)$_2$), 3.63 (q, 2H, C-21 —OCH$_2$CH$_3$, J=6 Hz), 4.03–4.60 (m, 3H, C-21 CH$_2$ and C-11 CH), 5.87 (s, 1H, C-4 CH), 6.72 (d, 2H, aromatic, J=9 Hz) and 7.08 (d, 2H, aromatic, J=9 Hz). MS (EI) m/z (relative intensity): 519 (M$^+$, 34), 459 (4.5), 372 (7.4), 134 (18) and 121 (100). Anal. Calad. for C$_{32}$H$_{41}$O$_5$N: C, 73.95; H, 7.96; N, 2.70; Found: C, 73.84; H, 8.20; N, 2.65.

Example XI

This example illustrates the preparation and properties of 17α,21-diacetoxy-11β-(4-N,N-dimethylaminophenyl)-19-norpregna-4,9-diene-3,20-dione 3-oxime as a mixture of syn and anti-isomers (47):

A solution of the diacetate (15, 0.5 g, 0.937 mmol) and hydroxylamine hydrochloride (0.651 g, 937 mmol) in absolute ethanol (25 mL) was stirred at room temperature under nitrogen. After 2.5 hr, TLC (10% acetone in CH$_2$Cl$_2$) indicated a complete reaction. The reaction mixture was diluted with H$_2$O (200 mL), adjusted to a pH 7 with saturated NaHCO$_3$ solution, and extracted with CH$_2$Cl$_2$ (3×). The organic fractions were washed with H$_2$O (2×) and brine (1×), combined, dried (Na$_2$SO$_4$), filtered and concentrated in vacuo to give 0.56 g of residue as a foam. Purification by flash chromatography (5% acetone/CH$_2$Cl$_2$) followed by precipitation from ether solution with pentane gave 0.3 g of the oxime (47) in 58% as an off-white amorphous powder. Analysis by HPLC on a NovaPak C$_{18}$ column eluting with CH$_3$CN:H$_2$O:Et3N 45:55:0.033 at a flow rate of 2 mL per min at λ=274 nm indicated approximately 98% purity consisting of a 32:68 mixture of the syn- and anti-isomers. Analysis by NMR indicated a syn:anti ratio of 43:57: mp=sinters at 151° C., and then decomposes. FTIR (KBr, diffuse reflectance) ν$_{max}$ 2946, 1737, 1612 and 1518 cm$^{-1}$. NMR (CDCl$_3$) δ 0.40 (s, 3H, 18-CH$_3$), 3.93 (s, 6H, NMe$_2$) 4.40 (br. s, 1H, 11α-H), 4.87 (dd, J$_1$=29.7 Hz, J$_2$=18 Hz, 2H, 21-CH$_2$OAc), 5.97 (s, 0.57H, 4-CH for anti-isomer), 6.63 (s, 0.43H, 4-CH for syn-isomer), 6.70 (d, 2H, J=9 Hz, 3' and 5' aromatic CH) and 7.10 (d, 2H, J=9 Hz, 2' and 6' aromatic CH). MS (EI) m/z (relative intensity): 549((M+H)$^+$, 63) and 275 (100).

Example XII

This example illustrates the preparation and properties of 17α-acetoxy-21-methoxy-11β-(4-N,N-dimethylaminophenyl)-19-norpregna-4,9-diene-3,20-dione 3-oxime as a mixture of syn and anti-isomers (48):

A solution of the 21-methoxy compound (38, 0.1 g, 0.2 mmol) and hydroxylamine hydrochloride (0.139 g, 2 mmol) in absolute ethanol (5 mL) was stirred at room temperature under nitrogen. After 1 hr, TLC (10% acetone in CH$_2$Cl$_2$) indicated a complete reaction. The reaction mixture was diluted with H$_2$O, adjusted to a pH of 7 with saturated NaHCO$_3$ solution, and extracted with CH$_2$Cl$_2$ (3×). The organic fractions were washed with H$_2$O (2×) and brine (1×), combined, dried over Na$_2$SO$_4$ filtered and concentrated in vacuo to give the crude product as a foam. This material was combined with 0.12 g additional crude product in a previous batch and the total amount (0.21 g) was purified by flash chromatography (15% acetone/CH$_2$Cl$_2$) followed by trituration with pentane to give 0.12 g of the oxime (48) in 58% yield as a white amorphous powder. Analysis by HPLC on a NovaPak $C_{18}$ column eluting with MeOH:$H_2$O:Et$_3$N 65:35:0.0033 at a flow rate of 1 mL/min at λ=276 nm indicated approximately 97% purity of a mixture of the syn- and anti-isomers. The retention times of the two isomers were too close together ($R_T$=8.8 and 9.2 min) to give an accurate integration ratio. Analysis by NMR indicated a syn:anti ratio of 26:74 mp: sinters at 142° C. and melts at 146–162° C. FTIR (KBr, diffuse reflectance) $v_{max}$ 2938, 1733, 1613 and 1517 cm$^{-1}$. NMR (300 MHZ, CDCl$_3$) δ 0.36 (s, 3H, 18-CH$_3$), 2.10 (s, 3H, 17α-OAc), 2.89 (s, 6H, NMe$_2$), 3.41 (s, 3H, OCH$_3$), 4.10 (d, 1H 21-CH$_2$, J=16.8 Hz), 4.30 (m, 2H, 11α-H plus 21-CH$_2$), 5.88 (s, 0.74H, 4-CH for anti-isomer), 6.53 (s, 0.26H, 4-CH for syn-isomer), 6.62 (d, 2H, 3' and 5' aromatic CH, J=8.7 (Hz) and 6.99 (d, 2H, 2' and 6' aromatic CH, J=8.7 Hz). MS (EI) m/z (relative intensity): 521((M+H)$^+$, 100) and 261 67).

B. Biological Properties of the Compounds of Formula I

MATERIALS AND METHODS

AntiMcGinty Test

Immature female rabbits of the New Zealand White breed (approx. 1 kg body weight) were maintained under standard laboratory conditions and received a subcutaneous injection of 5 μg estradiol in 10% ethanol/sesame oil daily for 6 consecutive days. Twenty-four hours after the last injection of estradiol (day 7) animals underwent sterile abdominal surgery to ligate a 3–4 cm segment of both uterine horns. The experimental compound in appropriate solvent (usually 10% ethanol/sesame oil) was injected intraluminally into the ligated segment of one uterine horn and the vehicle alone into the ligated segment of the contralateral horn. Injection volume was limited to 0.1 ml and care was taken to prevent leakage. A stimulating dose of progesterone (267 μg/day) was administered subcutaneously to each rabbit daily for the next three days (days 7, 8 and 9) for the purpose of inducing endometrial proliferation. All animals were sacrificed on day 10 for the removal of the uterus where a segment central to the ligatures was removed and fixed in 10% neutral buffered formalin and submitted for histological processing. Five micron sections stained with hematoxylin and eosin (H&E) were evaluated microscopically for the degree of endometrial glandular proliferation according to the method of McPhail. The percent inhibition of endometrial proliferation for each rabbit was calculated and the mean of the group of five animals recorded.

AntiClauberg Test

Immature female rabbits of the New Zealand White breed (approx. 1 kg body weight) were maintained under standard laboratory conditions and received a subcutaneous injection of 5 μg estradiol in 10% ethanol/sesame oil daily for 6 consecutive days. Twenty-four hours after the last dose of estradiol (day 7) animals received progesterone by subcutaneous injection (160 μg/day) and the experimental compound in appropriate vehicle (usually 10% ethanol/sesame oil) orally or subcutaneously for five consecutive days. One group of rabbits received progesterone only. Twenty-four hours after the last dose all animals were sacrificed for removal of the uterus which was cleaned of all fat and connective tissue, weighed to the nearest 0.2 mg and placed in 10% neutral buffered formalin for subsequent histological processing. Five micron sections stained with hematoxylin and eosin (H&E) were evaluated microscopically for the degree of endometrial glandular proliferation according to the method of McPhail. The percent inhibition of endometrial proliferation at each dose level of the experimental compound was derived by comparison with the progesterone-stimulated animals alone.

Relative Binding Affinities for the Progesterone and Glucocorticoid Receptors

Uteri and thymus glands were obtained from estradiol-primed immature female rabbits of the New Zealand White strain. Tissues were excised and immediately place in ice cold TEGDM buffer (10 mM Tris, pH 7.4; 1.5 mM EDTA; 10% glycerol vol/vol/; 1 mM dithiothreitol [DTT]; and 20 mM sodium molybdate). The tissues were dissected free of connective tissue and fat, weighted and minced finely. Minced tissues were homogenized in 3 volumes TEGDM/gm with four 10 second bursts of a VirTis Cyclone set at half maximum speed with a 30 second cooling period (in ice) between bursts. Homogenates were centrifuged at 109,663 g at 4° C. for 1 hour to yield the soluble cytosol fraction. Aliquots of cytosol were snap frozen and stored at −75° C.

All binding assays were carried out at 2–6° C. for 16–18 hours. The following radioactive ligands were used: [1,2-$^3$H(N)]-progesterone (50.0 Ci/mmole) for the progesterone receptor PR) and [6,7-$^3$H(N)]-dexamethasone (39.2 Ci/mmole) for the glucocorticoid receptor (GR). For the progesterone receptor RBA assays 0.02 ml uterine cytosol or TEDGM buffer, 0.05 ml of various concentrations of test compounds or progesterone, 0.13 ml TEGDM buffer and 0.05 ml [$^3$H]-progesterone were added to duplicate tubes. For the glucocorticoid receptor RBA assays 0.1 ml thymus cytosol or TEDGM buffer, 0.05 ml of various concentrations of test compounds or dexamethasone, 0.05 ml TEGDM buffer and 0.05 ml [$^3$,H]-dexamethasone were added to duplicate tubes. The concentrations of the test compounds, progesterone and dexamethasone ranged from 0.5 to 500 nM. Total binding was measured at radioactive ligand concentrations of 3.5 nM and nonspecific binding was measured in the presence of a 200-fold molar excess of unlabeled progesterone (PR) or dexamethasone (GR), respectively.

In all incubations bound and free ligand were separated using dextra-coated charcoal (DCC). A 0.1 ml aliquot of DCC (0.5% charcoal/0.05% Dextran T-70) was added to each tube. The tubes were vortexed and incubated on ice for 10 minutes. Five tenths ml TEG buffer (without DTT or molybdate) was then added to all tubes to improve supernatant recovery following centrifugation. The charcoal was pelleted by centrifugation at 2,100 g for 15 minutes at 4° C. The supernatants containing the [$^3$H]-steroid receptor complexes were decanted into vials contain 4 ml Optifluor (Packard Instrument Co.), vortexed, equilibrated in a liquid scintillation counter for 30 minutes and then counted for 2 minutes. This provided the quantity of receptor bound [$^3$H]-steroid at each competitor concentration.

The $EC_{50}$ (Effective Concentration) for each standard curve and each of the compound curves was determined by entering the counting data (receptor bound [$^3$H]-progesterone or [$^3$H]-dexamethasone into a four parameter sigmoidal computer program (RiaSmart® Immunoassay Data Reduction Program, Packard Instrument Co., Meriden, Conn. The RBA for each test compound was calculated using the following equation:

$$RBA = EC_{50} \frac{\text{Standard}}{EC_{50} \text{ Test Compound}} \times 100$$

where $EC_{50}$ Standard=molar concentration of unlabeled progesterone or dexamethasone required to decrease bound [$^3$H]-progesterone (PR) or [$^3$H]-dexamethasone (GR) to 50% of the respective buffer control (100% bound ligand) and $EC_{50}$ Test Compound=molar concentration of test compound required to decrease bound [$^3$H]-progesterone (PR) or [$^3$]-dexamethasone (GR) to 50% of the respective buffer control (100% bound ligand).

RESULTS

Results of the antiMcGinty and oral antiClauberg tests as well as the relative binding affinities of these compounds are shown in Table 1, infra. Compared to the lead compound (CDB-2914, 21-H), the 21-acetoxy (15) and the 21-methoxy (38) analogs exhibited 2.79 and 3.61 times, respectively, the antiprogestational potency as assessed by the oral antiClauberg test with a substantial reduction in glucocorticoid binding affinity. Further, the results of the anti McGinty test of the 21-acetoxy analog (15) following intraluminal administration closely paralleled those observed in the antiClauberg test following oral dosing. Since mifepristone (CDB-2477) is frequently used as a reference standard, Table 2, infra, contains data comparing the antiprogestational activity and relative binding affinity for the progesterone and glucocorticoid receptors of CDB-2914 with this standard. Recent studies have shown a good correlation between relative binding affinity for the glucocorticoid receptor and a biological test based upon the antagonism of dexamethasone-induced thymus involution in adrenalectomized male rats.

The halogenated analogs (13, 14A, 14B) did not show significant differences in antiprogestational activity nor relative binding affinity to the progesterone receptor from the lead compound, CDB-2914. Other 21-substituted analogs generally exhibited reduced antiprogestational activity with the exception of the cypionate (40) which was about 50% more potent in the anticlauberg test. This may be due to hydrolysis to the corresponding 21-hydroxy compound. However, the presence of additional bulkiness at position 21 does not always favor an increase in biological activity (see 14B) and enhanced relative binding affinity for the progesterone receptor was not necessarily indicative of greater antiprogestational activity (see 12). Thus the window of opportunity for enhanced antiprogestational activity with a reduction in relative binding affinity for the glucocorticoid receptor for 21-substituted analogs of the lead compound (CDB-2914) is highly restricted and was identified only after numerous analogs had been synthesized and tested.

TABLE 1

ANTIPROGESTATIONAL ACTIVITY AND RELATIVE BINDING AFFINITY FOR THE PROGESTERONE AND GLUCOCORTICOID RECEPTORS

| COM-POUND | ANTIPROGESTATIONAL[1] | | RELATIVE BINDING AFFINITY[2] | |
|---|---|---|---|---|
| | AntiMcGinty | AntiClauberg | Progesterone | Glucocorticoid |
| CDB-2914 | 100 | 100 | 122 | 114 |
| 12 | 26 | 29 | 261 | 32 |
| 13 | 103 | 80 | 125 | 109 |
| 14A | 75 | 68 | 127 | 90 |
| 14B | 71 | | 130 | 175 |
| 15 | 300 | 279 | 103 | 51 |
| 16 | >2 | | 6 | 77 |
| 17 | 65 | | 37 | 54 |
| 28 | 32 | | 129 | 126 |
| 38 | | 361 | 103 | 52 |
| 40 | | 155 | 74 | 37 |
| 41 | | 140 | 62 | 71 |
| 46 | | 130–210 | 83 | 46 |

[1]Antiprogestational Activity
AntiMcGinty: see text; CDB-2914 = 100 (assigned)
AntiClauberg, oral: see text; CDB-2914 = 100 (assigned)
[2]Relative Binding Affinity
Progesterone receptor (estrogen-primed rabbit uterus) progesterone = 100%
Glucocorticoid receptor (estrogen-primed rabbit thymus) dexamethasone = 100%

TABLE 2

RELATIVE BINDING AFFINITIES AND ANTIPROGESTATION ACTIVITY OF CDB-2914 AND MIFEPRISTONE (CDB-2477)

| | RELATIVE BINDING AFFINITY | | ANTIPROGESTATIONAL ACTIVITY | |
|---|---|---|---|---|
| DRUG | PROGESTERONE[1] | GLUCOCORTICOID[2] | ANTI-MCGINTY[3] | ANTI-CLAUBERG[4] |
| CDB-2914 | 114 ± (n = 18) | 127 ± 24 (n = 12) | 0.56 | 3.27 |
| CDB-2477 | 150 ± 17 (n = 11) | 221 ± 35 (n = 6) | 1.0 (assigned) | 1.0 (assigned) |

[1]Progesterone = 100%; immature estrogen-primed rabbit uterus
[2]Dexamethasone = 100%; immature estrogen-primed rabbit thymus
[3]Intraluminal administration to estrogen-primed immature rabbits; CDB-2477 = 1.0 (assigned)
[4]Oral administration to estrogen-primed immature rabbits; CDB-2477 = 1.0 (assigned)

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A compound having the general formula:

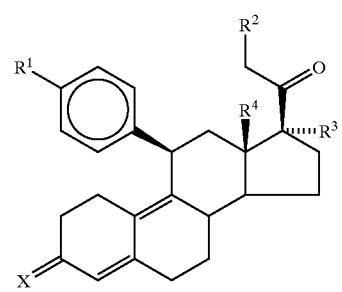

in wherein:

$R^1$ is a member selected from the group consisting of —N(CH$_3$)$_2$ and —NHCH$_3$;

$R^2$ is a member selected from the group consisting of halogen, alkyl, acyl, hydroxy, alkoxy, acyloxy, alkylcarbonate, cypionyloxy, S-alkyl and S-acyl;

$R^3$ is a member selected from the group consisting of alkyl, hydroxy, alkoxy and acyloxy;

$R^4$ is a member selected from the group consisting of hydrogen and alkyl; and

X is a member selected from the group consisting of =O and =N—OR$^5$, wherein R$^5$ is a member selected from the group consisting of hydrogen and alkyl;

with the proviso that if X is =O, R$^1$ is —N(CH$_3$)$_2$, R$^2$ is hydroxy and R$^4$ is alkyl, then R$^3$ is other than hydroxy.

2. A compound in accordance with claim 1 in which:

R$^1$ is —N(CH$_3$)$_2$.

3. A compound in accordance with claim 1 in which:
$R^2$ is halogen.

4. A compound in accordance with claim 1 in which:
$R^2$ is alkoxy.

5. A compound in accordance with claim 1 in which:
$R^3$ is acyloxy.

6. A compound in accordance with claim 1 in which:
$R^4$ is alkyl.

7. A compound in accordance with claim 1 in which:
X is =O.

8. A compound in accordance with claim 1 in which:
X is =N—$OR^5$.

9. A compound in accordance with claim 1 in which:
$R^1$ is —$N(CH_3)_2$;
$R^2$ is halogen;
$R^3$ is acyloxy;
$R^4$ is alkyl; and
X is =O.

10. A compound in accordance with claim 9 in which:
$R^2$ is F.

11. A compound in accordance with claim 9 in which:
$R^2$ is Br.

12. A compound in accordance with claim 9 in which:
$R^2$ is Cl.

13. A compound in accordance with claim 9 in which:
$R^4$ is methyl.

14. A compound in accordance with claim 1 in which:
$R^1$ is —$N(CH_3)_2$;
$R^2$ is alkyl;
$R^3$ is acyloxy;
$R^4$ is alkyl; and
X is =O.

15. A compound in accordance with claim 1 in which:
$R^1$ is —$N(CH_3)_2$;
$R^2$ is alkoxy;
$R^3$ is acyloxy;
$R^4$ is alkyl; and
X is =O.

16. A compound in accordance with claim 15 in which:
$R^2$ is methoxy.

17. A compound in accordance with claim 15 in which:
$R^2$ is ethoxy.

18. A compound in accordance with claim 15 in which:
$R^3$ is acetoxy.

19. A compound in accordance with claim 1 in which:
$R^1$ is —$N(CH_3)_2$;
$R^2$ is hydroxy;
$R^3$ is acyloxy;
$R^4$ is alkyl; and
X is =O.

20. A compound in accordance with claim 1 in which:
$R^1$ is —$N(CH_3)_2$;
$R^2$ and $R^3$ are both acyloxy;
$R^4$ is alkyl; and
X is =O.

21. A compound in accordance with claim 20 in which:
$R^2$ and $R^3$ are both acetoxy.

22. A compound in accordance with claim 1 in which:
$R^1$ is —$N(CH_3)_2$;
$R^2$ is S-acyl;
$R^3$ is a member selected from the group consisting of hydroxy and acyloxy;
$R^4$ is alkyl; and
X is =O.

23. A compound in accordance with claim 1 in which:
$R^1$ is —$N(CH_3)_2$;
$R^2$ is cypionyloxy;
$R^3$ is acetoxy;
$R^4$ is alkyl; and
X is =O.

24. A compound in accordance with claim 1 in which:
$R^1$ is —$N(CH_3)_2$;
$R^2$ is methoxy;
$R^3$ is acetoxy;
$R^4$ is alkyl; and
X is =N—$OR^5$.

25. A compound in accordance with claim 1 in which:
$R^1$ is —$N(CH_3)_2$;
$R^2$ and R3 are both acetoxy;
$R^4$ is alkyl; and
X is =N—$OR^5$.

26. A pharmaceutical composition comprising an effective amount of a compound of claim 1 and a pharmaceutically acceptable excipient.

27. A method of producing an antiprogestational effect in a patient, said method comprising administering to said patient an effective amount of a compound of claim 1.

28. A method of inducing menses in a patient, said method comprising administering to said patient an effective amount of a compound of claim 1.

29. A method of treating endometriosis, said method comprising administering to said patient an effective amount of a compound of claim 1.

30. A method of treating dysmenorrhea, said method comprising administering to said patient an effective amount of a compound of claim 1.

31. A method of treating endocrine hormone-dependent tumors, said method comprising administering to said patient an effective amount of a compound of claim 1.

32. A method of treating uterine fibroids in a patient, said method comprising administering to said patient an effective amount of a compound of claim 1.

33. A method of inhibiting uterine endometrial proliferation in a patient, said method comprising administering to said patient an effective amount of a compound of claim 1.

34. A method of inducing labor, said method comprising administering to a patient an effective amount of a compound of claim 1.

35. A method of contraception, said method comprising administering to a patient an effective amount of a compound of claim 1.

36. A method of postcoital contraception, said method comprising administering to a patient an effective amount of a compound of claim 1.

* * * * *

UNITED STATES PATENT AND TRADEMARK OFFICE
CERTIFICATE OF CORRECTION

PATENT NO.        : 6,861,415 B2
APPLICATION NO. : 09/180132
DATED              : March 1, 2005
INVENTOR(S)      : Hyun K. Kim et al.

It is certified that error appears in the above-identified patent and that said Letters Patent is hereby corrected as shown below:

Title page, under the Abstract, item (57), line 3, correct the formula to read:

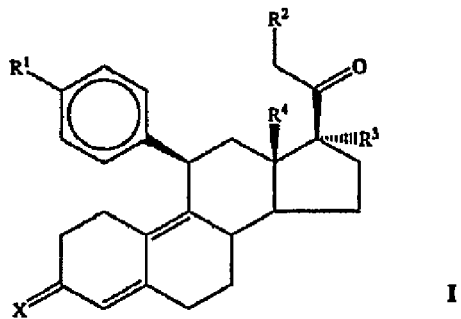

Figure 1B:
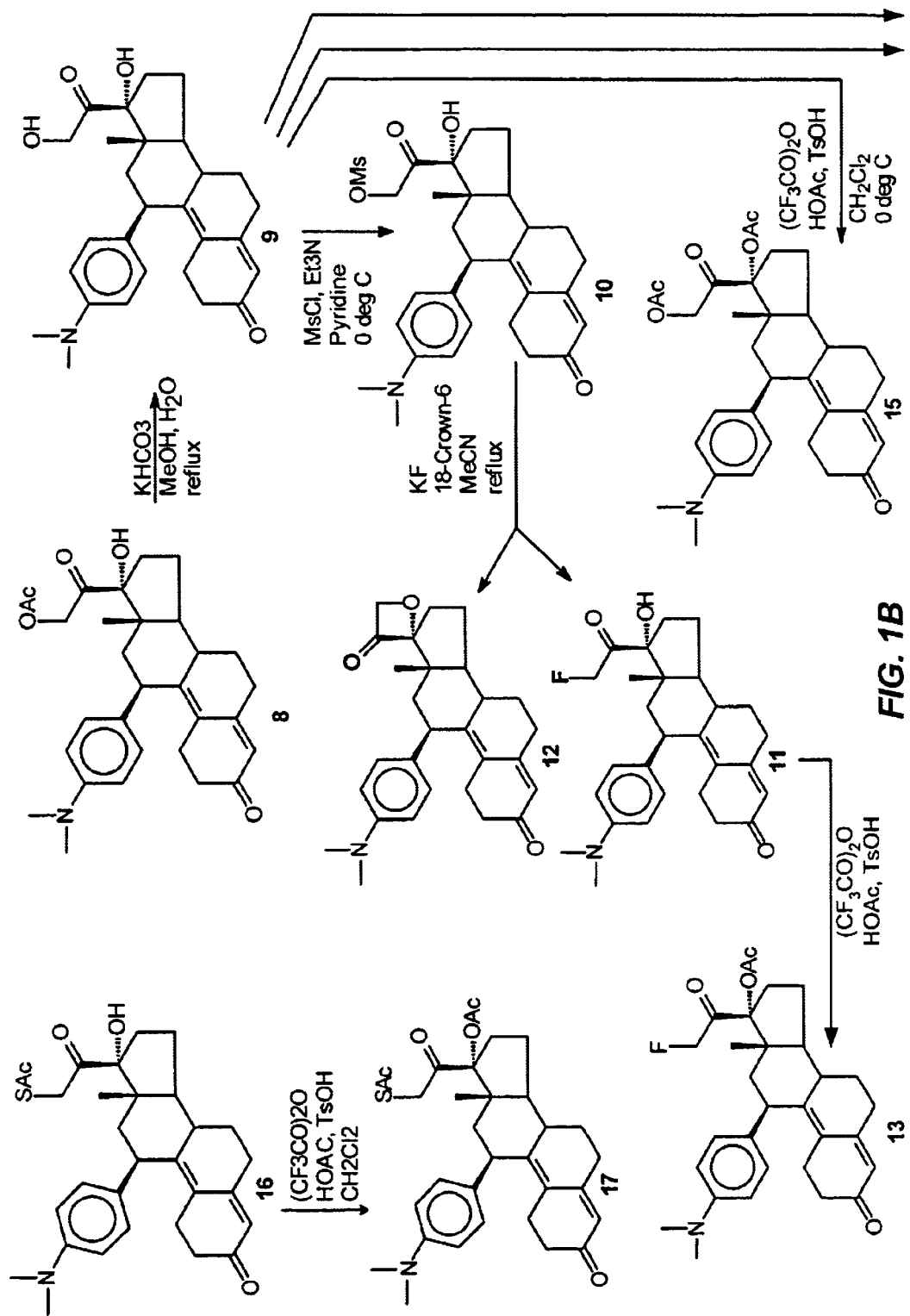
Figure 1C:
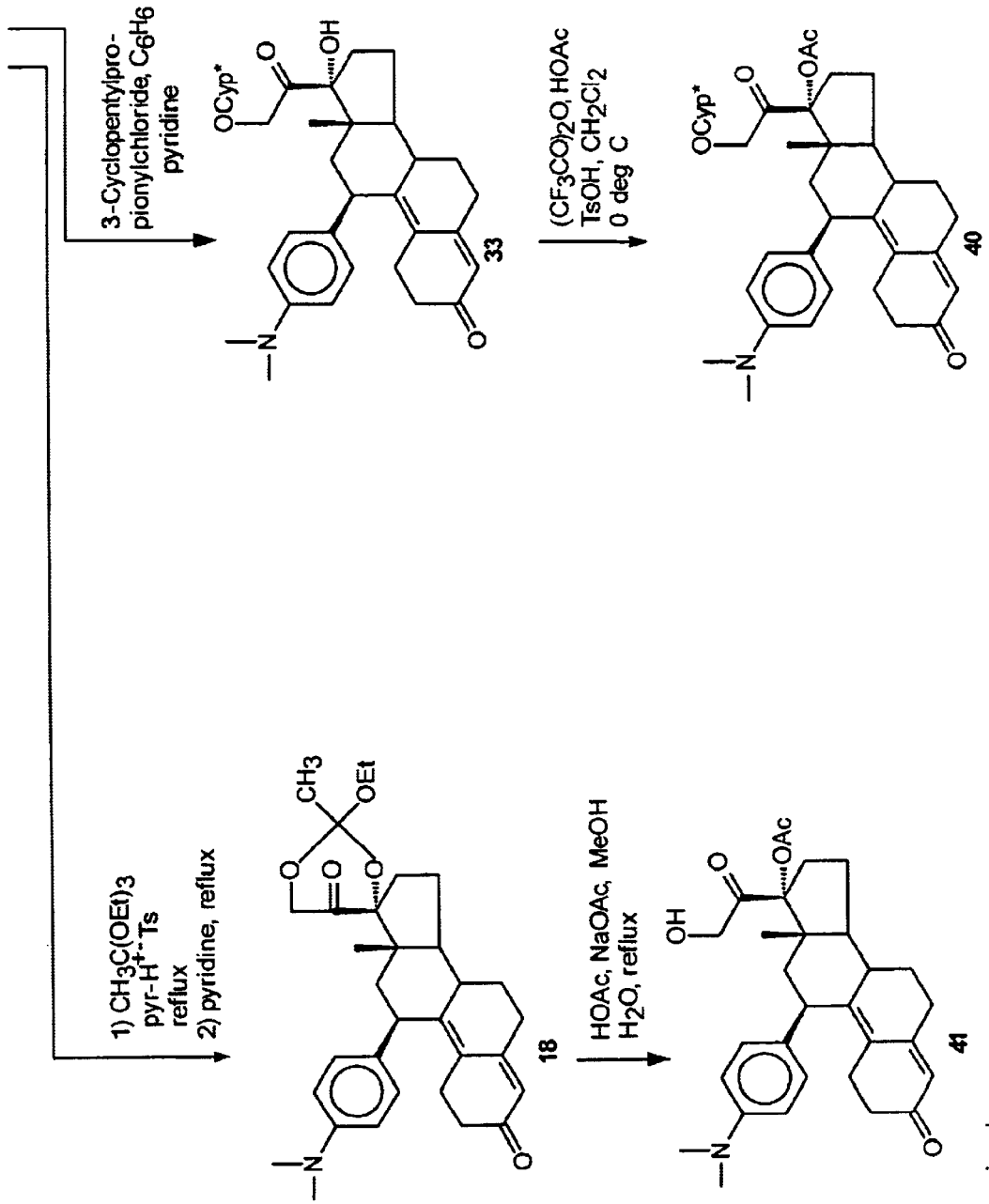

Drawing sheet 1 of 5 Fig. 1A, between formulas 1 and 2, replace "Me₃SiC" with -- Me₃SiCl --.

Drawing sheet 1 of 5 Fig. 1A, between formulas 2 and 3, replace "CF₃)₂CO" with -- (CF₃)₂CO --.

Column 2, line 17 under Summary of the Invention, correct the formula to read:

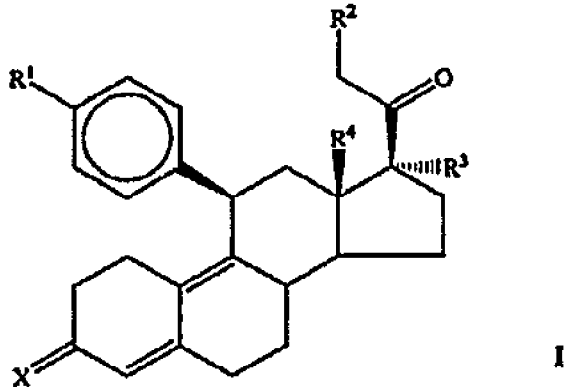

UNITED STATES PATENT AND TRADEMARK OFFICE
CERTIFICATE OF CORRECTION

PATENT NO. : 6,861,415 B2
APPLICATION NO. : 09/180132
DATED : March 1, 2005
INVENTOR(S) : Hyun K. Kim et al.

It is certified that error appears in the above-identified patent and that said Letters Patent is hereby corrected as shown below:

Column 3, line 3, under Detailed Description of the Invention and Preferred Embodiments, correct the formula to read:

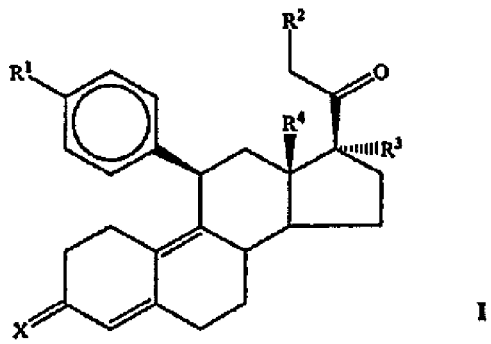

Signed and Sealed this

Ninth Day of January, 2007

JON W. DUDAS
*Director of the United States Patent and Trademark Office*